(12) United States Patent
Qasim et al.

(10) Patent No.: US 12,410,444 B2
(45) Date of Patent: Sep. 9, 2025

(54) MINIMAL PROMOTER

(71) Applicant: UCL Business Ltd, London (GB)

(72) Inventors: Waseem Qasim, London (GB);
Christos Georgiadis, London (GB);
Roland Preece, London (GB); Soragia Athina Gkazi, London (GB)

(73) Assignee: UCL Business Ltd, London (GB)

( * ) Notice: Subject to any disclaimer, the term of this patent is extended or adjusted under 35 U.S.C. 154(b) by 987 days.

(21) Appl. No.: 17/593,184

(22) PCT Filed: Mar. 13, 2020

(86) PCT No.: PCT/GB2020/050651
§ 371 (c)(1),
(2) Date: Sep. 10, 2021

(87) PCT Pub. No.: WO2020/183197
PCT Pub. Date: Sep. 17, 2020

(65) Prior Publication Data
US 2022/0154216 A1  May 19, 2022

(30) Foreign Application Priority Data
Mar. 14, 2019 (GB) .................................... 1903499

(51) Int. Cl.
| | |
|---|---|
| *C12N 15/86* | (2006.01) |
| *C12N 5/0783* | (2010.01) |
| *C12N 9/22* | (2006.01) |
| *C12N 15/11* | (2006.01) |
| *C12N 15/90* | (2006.01) |

(52) U.S. Cl.
CPC .......... *C12N 15/86* (2013.01); *C12N 5/0636* (2013.01); *C12N 9/22* (2013.01); *C12N 15/11* (2013.01); *C12N 15/907* (2013.01); *C12N 2310/20* (2017.05); *C12N 2740/15043* (2013.01); *C12N 2800/80* (2013.01); *C12N 2830/34* (2013.01); *C12N 2830/46* (2013.01)

(58) Field of Classification Search
CPC ........ C12N 15/86; C12N 5/0636; C12N 9/22; C12N 15/11; C12N 15/907; C12N 2310/20; C12N 2740/15043; C12N 2800/80; C12N 2830/34; C12N 2830/46
See application file for complete search history.

(56) References Cited

U.S. PATENT DOCUMENTS

2018/0155712 A1* 6/2018 Feldstein ........... C12N 15/1093

FOREIGN PATENT DOCUMENTS

| WO | 03/057840 A2 | 7/2003 |
| WO | 2005/007875 A2 | 1/2005 |
| WO | 2018/115887 A1 | 6/2018 |

OTHER PUBLICATIONS

GenBank Accession JN255693, Homo sapiens U6 snRNA gene, complete sequence (May 31, 2012). (Year: 2012).*
Adamson et al., "A Multiplexed 1-24 Single-Cell CRISPR Screening Platform Enables Systematic Dissection of the Unfolded Protein Response", Cell, vol. 167, No. 7, Dec. 15, 2016 (Dec. 15, 2016), p. 1867, Elsevier Amsterdam, NL.
Domitrovich and Kunkel, "Multiple, dispersed human U6 small nuclear RNA genes with varied transcriptional efficiencies", (2003), Nucleic Acids Research; 31(9): 2344-2352.
Georgiadis et al., "Long Terminal 1-24 Repeat CRISPR-CAR-Coupled "Universal" T Cells Mediate Potent Anti-leukemic Effects", Molecular Therapy : The Journal of The American Society of Gene Therapy, vol. 26, No. 5, May 1, 2018 (May 1, 2018), pp. 1215-1227.
Gilbert et al., "CRISPR-Mediated Modular RNA-Guided Regulation of Transcription in Eukaryotes", (2013), Cell, Jul. 18; 154(2): 442-451.
Myslinski et al., "Optimal tRNA(Ser)Sec gene activity requires an upstream SPH motif", (1992), Nucleic Acids Research; 20(2): 203-209.
Myslinski et al., "An unusually compact 1,2,4-7, external promoter for RNA polymerase III transcription of the human H1RNA gene", Nucleic Acids Research, Oxford University 16,20 Press, GB, vol. 29, No. 12, Jun. 15, 2001 (Jun. 15, 2001), pp. 2502-2509.
Preece et al., "'Mini' U6 Pol III promoter exhibits nucleosome redundancy and supports multiplexed coupling of CRISPR/Cas9 effects", Gene Therapy, Mar. 20, 2020.
Stunkel et al., "A Nucleosome Positioned in the Distal Promoter Region Activates Transcription of the Human U6 Gene", Molecular and Cellular Biology, vol. 17, Aug. 1, 1997 (Aug. 1, 1997), pp. 4397-4405.
Ye K, et al., "Pindel: a pattern growth approach to detect break points of large deletions and medium sized insertions from paired-end short reads" (2009), Bioinformatics, Nov 1; 25(21): 2865-71.
Zhao et al., "A Positioned Nucleosome on the Human U6 Promoter Allows Recruitment of SNAPc by the Oct-1 POU Domain", (2001), Mol Cell, Mar; 7(3): 539-49.

* cited by examiner

*Primary Examiner* — Tracy Vivlemore
*Assistant Examiner* — Eric J Rogers
(74) *Attorney, Agent, or Firm* — Norton Rose Fulbright US LLP

(57) ABSTRACT

The invention relates to a minimal U6 pol III promoter. The invention also concerns a nucleic acid construct comprising the minimal U6 pol III promoter, a vector comprising the minimal U6 pol III promoter, methods involving the minimal U6 pol III promoter, and uses for the minimal U6 pol III promoter.

17 Claims, 15 Drawing Sheets

Specification includes a Sequence Listing.

A. ΔU6 Pol III promoters:

i. Wild type U6: 249bp

138bp spacer ii. Minimal U6: 111bp iii. TATA alone: 46bp iv. PSE+TATA: 75bp v. SPH-OCT+TATA: 82bp

MINIMAL PROMOTER

CROSS REFERENCE TO RELATED APPLICATIONS

This application is a national phase under 35 U.S.C. § 371 of International Application No. PCT/GB2020/050651, filed Mar. 13, 2020, which claims the benefit of priority to Great Britain Patent Application Serial No. 1903499.0, filed Mar. 14, 2019, the entire contents of each of which are hereby incorporated by reference in their entirety.

INCORPORATION OF SEQUENCE LISTING

The instant application contains a Sequence Listing, named "KEMP.P0122US_ST25.txt" (6,417 bytes; created Mar. 27, 2025), which has been submitted in ASCII text format and is hereby incorporated by reference in its entirety.

FIELD OF THE INVENTION

The invention relates to a minimal U6 pol III promoter. The invention also concerns a nucleic acid construct comprising the minimal U6 pol III promoter, a vector comprising the minimal U6 pol III promoter, methods involving the minimal U6 pol III promoter, and uses for the minimal U6 pol III promoter.

BACKGROUND TO THE INVENTION

Type III RNA polymerase promoters are used in the art for the expression of RNA sequences. For instance, type III RNA polymerase promoters can be used to express siRNA or miRNA for use in RNA interference. Type III RNA polymerase promoters can also be used to express CRISPR guide sequences (sgRNA) for directing the effects of CRISPR guided DNA modification enzymes, such as Cas nucleases and deactivated Cas proteins coupled to deamination enzymes (base editors). Exemplary type III RNA polymerase promoters include H1 and U6 promoters. Each of these is around 300 bp in length. To function properly, H1 promoters and U6 promoters must contain a TATA box, a proximal sequence element (PSE), and a distal sequence element (DSE) comprising a conserved octamer sequence critical for protein binding.

To express an RNA sequence of interest in a cell using a type III RNA polymerase promoter, a vector containing a nucleic acid construct encoding the promoter and the sequence of interest is typically introduced to the cell. Viral vectors are often used in this regard. Viral vectors have a limited DNA insert capacity. That is, there is an upper limit to the size of the nucleic acid construct that can be incorporated to the vector. For example, an adeno-associated virus (AAV) vector can only tolerate insertion of a nucleic acid construct up to 5 kb in length. A lentiviral vector can only tolerate insertion of a nucleic acid construct up to 9 kb in length. This limits the length and/or number of transgenes that can be contained in a single vector.

The length and/or number of coded sequences that can be contained in a single vector can be increased by reducing the length of the type III RNA polymerase promoter controlling transcription of coded sequence(s). In essence, reducing the size of the promoter makes space for a larger sequence or a greater number of sequences. Shortened H1 promoters have been described (Myslinski, 2001). However, Zhao et al. (Mol Cell, 2001) demonstrated that in the natural human U6 promoter, an octamer element and the PSE only co-localise (and therefore achieve transcription) in the presence of nucleosomal effects encoded by an intervening sequence of around 150 bp in length. This has made the development of a shortened U6 promoter challenging.

SUMMARY OF THE INVENTION

The present inventors have demonstrated that, surprisingly, the nucleosomal region between the PSE and DSE can be shortened to create a "minimal" (i.e. shortened) U6 pol III promoter. The minimal U6 pol III promoter comprises a DSE, a PSE and TATA box and is capable of vector-mediated RNA expression. The minimal U6 pol III promoter may be less than half the size of the wild-type U6 pol III promoter. This is advantageous when the U6 pol III promoter RNA expression cassette is used in a vector that has a limited cargo capacity (i.e. an upper limit on the size of the nucleic acid construct that can be incorporated to the vector). Use of the minimal U6 pol III promoter effectively makes space in the vector, such that more and/or larger nucleic acid sequence(s) of interest can be comprised in the vector. For instance, the minimal U6 pol III promoter may be used in an RNA expression cassette that would otherwise reach the upper limit for incorporation to a vector to make the vector such that more nucleic acid sequences for RNA expression may be included in the expression cassette, In this way, multiplexed effects can be achieved.

There are many uses for the minimal U6 pol III promoter. The minimal U6 pol III promoter can, for example, be used as a basic tool for RNA expression. For instance, the minimal U6 pol III promoter can be used to express siRNA or miRNA sequences for use in RNA interference. The minimal U6 pol III promoter can, for example, be used in clinical applications. For instance, the minimal U6 pol III promoter can be used to express CRISPR guide RNA (sgRNA). As discussed in detail below, the minimal U6 pol III promoter can be used in the so-called "terminal" CRISPR approach that is the subject of International patent publication no. WO 2018/115887).

Accordingly, the present invention provides:

A U6 pol III promoter that is 74 bp to 117 bp in length and which comprises, from 5' to 3', a distal sequence element (DSE), a proximal sequence element (PSE) and a TATA box;

nucleic acid construct comprising the U6 pol III promoter of the invention;

a vector comprising the nucleic acid construct of the invention;

a method for delivering CRISPR guide sequences and a CRISPR guided DNA modification enzyme to a cell, comprising (a) introducing one or more CRISPR guide sequences to said cell using a nucleic acid construct that comprises a 3' LTR comprising a U6 pol III promoter of the invention operably linked to a sequence encoding said CRISPR guide sequence(s); and (b) separately delivering the CRISPR guided DNA modification enzyme to said cell of (a) by introducing into it a nucleic acid or protein sequence encoding said CRISPR guided DNA modification enzyme;

use of a nucleic acid construct that comprises a 3' LTR comprising a U6 pol III promoter of the invention operably linked to a sequence encoding a CRISPR guide sequence to: (a) disrupt expression of TCR and/or MHC class 1 in a cell; (b) introduce a nucleic acid sequence encoding a FcR that comprises (I) an extracellular domain that is capable of binding to a constant domain of an antibody and (II) a transmembrane domain and a cytoplasmic domain that are capable of supporting T cell activation into a cell; (c) introduce a nucleic acid sequence encoding a CAR into a cell, optionally wherein the CAR is specific for CD2, CD7, CD10, CD19, CD20, CD22, CD30, CD33, CD45, CD123, erb-B2, CEA, IL13R, Ror, kappa light chain, TCR-beta constant 1, TCR-beta constant 2, MAGE-A1, MUC1, PSMA, VEGF-R, Her2, or CAIX; (d) introduce a nucleic acid sequence encoding a CAR into a cell and to disrupt expression of TCR and/or MHC class 1 in the cell, optionally wherein the CAR is specific for CD2, CD7, CD10, CD19, CD20, CD22, CD30, CD33, CD45, CD123, erb-B2, CEA, IL13R, Ror, kappa light chain, TCR-beta constant 1, TCR-beta constant 2, MAGE-A1, MUC1, PSMA, VEGF-R, Her2, or CAIX; (e) introduce a nucleic acid sequence encoding a recombinant TCR (rTCR) into a cell and to disrupt expression of endogenous TCR in the cell; (f) introduce a nucleic acid sequence encoding a restriction factor into a cell and to disrupt expression of CCR5 in the cell, optionally wherein the restriction factor is TRIM5CypA; (g) disrupt expression of a locus controlling a gain of function mutation in a cell and to introduce a nucleic acid sequence encoding a replacement protein into the cell; (h) disrupt expression of a locus controlling a transgene silencing pathway in a cell, optionally wherein the vector comprises a nucleic acid sequence encoding a transgene silenced by the pathway; or (i) disrupt expression of a locus controlling a checkpoint inhibitor pathway in a cell and to introduce a nucleic acid sequence encoding a suicide into the cell;

a method for generating T cells that comprise a nucleic acid sequence encoding a CAR and have disrupted TCR and/or MHC class 1 expression, comprising: (a) providing one or more T cells; (b) introducing into one or more of said T cells of (a) a nucleic acid sequence encoding a CAR; and (c) disrupting expression of TCR and/or MHC class 1 in said T cells of (b), wherein, in (c), the expression of TCR and/or MHC class 1 is disrupted by: (i) introducing one or more CRISPR guide sequences to said T cells of (b) using a nucleic acid construct that comprises a 3' LTR comprising a U6 pol III promoter of the invention operably linked to a sequence encoding said CRISPR guide sequence(s); and (ii) separately delivering a CRISPR guided DNA modification enzyme to said T cells of (b) by introducing into them a nucleic acid or protein sequence encoding said CRISPR guided DNA modification enzyme; and a method for generating universal antibody dependent cord T cells (U-ACTs), comprising: (a) providing a sample of cord blood; (b) separating cells that express CD62L from the sample, wherein the cells that express CD62L comprise cord blood T cells; (c) introducing into one or more of said cord blood T cells of (b) a nucleic acid sequence encoding an Fc-Receptor (FcR) that comprises (I) an extracellular domain that is capable of binding to a constant domain of an antibody and (II) a transmembrane domain and a cytoplasmic domain that are capable of supporting T cell activation; and (d) disrupting expression of T cell receptor and MHC class 1 in said cord blood T cells of (c), wherein, in (d), the expression of T cell receptor and/or MHC class 1 is disrupted by: (i) introducing one or more CRISPR guide sequences to said cord blood T cells of (c) using a nucleic acid construct that comprises a 3' LTR comprising a U6 pol III promoter of the invention operably linked to a sequence encoding said CRISPR guide sequence(s); and (ii) separately delivering a CRISPR guided DNA modification enzyme to said cord blood T cells of (c) by introducing into them a nucleic acid or protein sequence encoding said CRISPR guided DNA modification enzyme.

DESCRIPTION OF THE SEQUENCE LISTING

Figure 1:
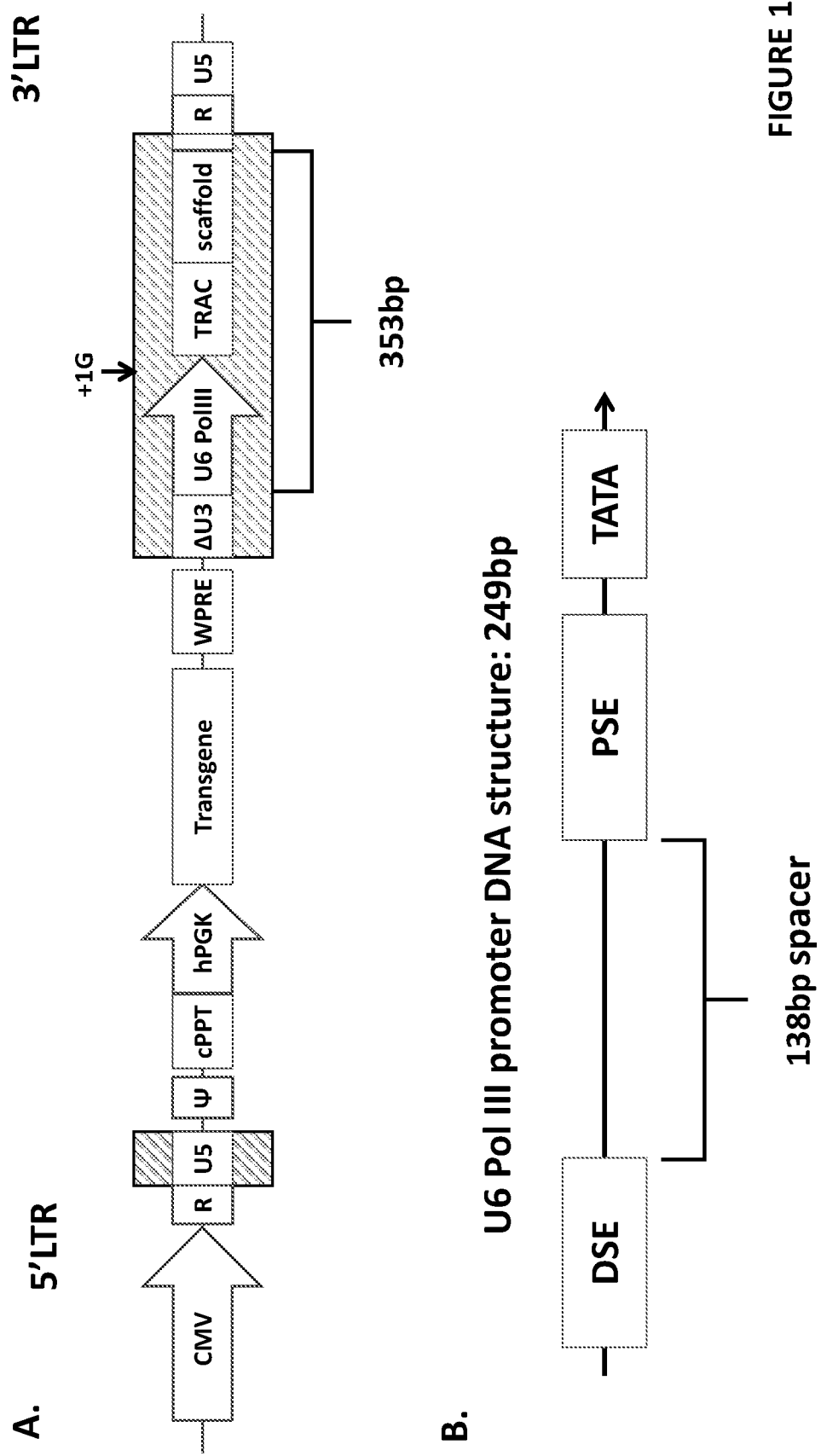
FIG. 1—Terminal lentiviral vector configuration: A) Schematic representation of a Terminal lentiviral vector expressing a transgene from a Pol II hPGK promoter and a T cell receptor alpha constant (TRAC) specific sgRNA from a Pol III U6 promoter. B) DNA structure of the Pol III U6 promoter used to express the sgRNA, consisting of a distal sequence element (DSE), spacer sequence (138 bp), proximal sequence element (PSE), and a TATA box.
Figure 2:
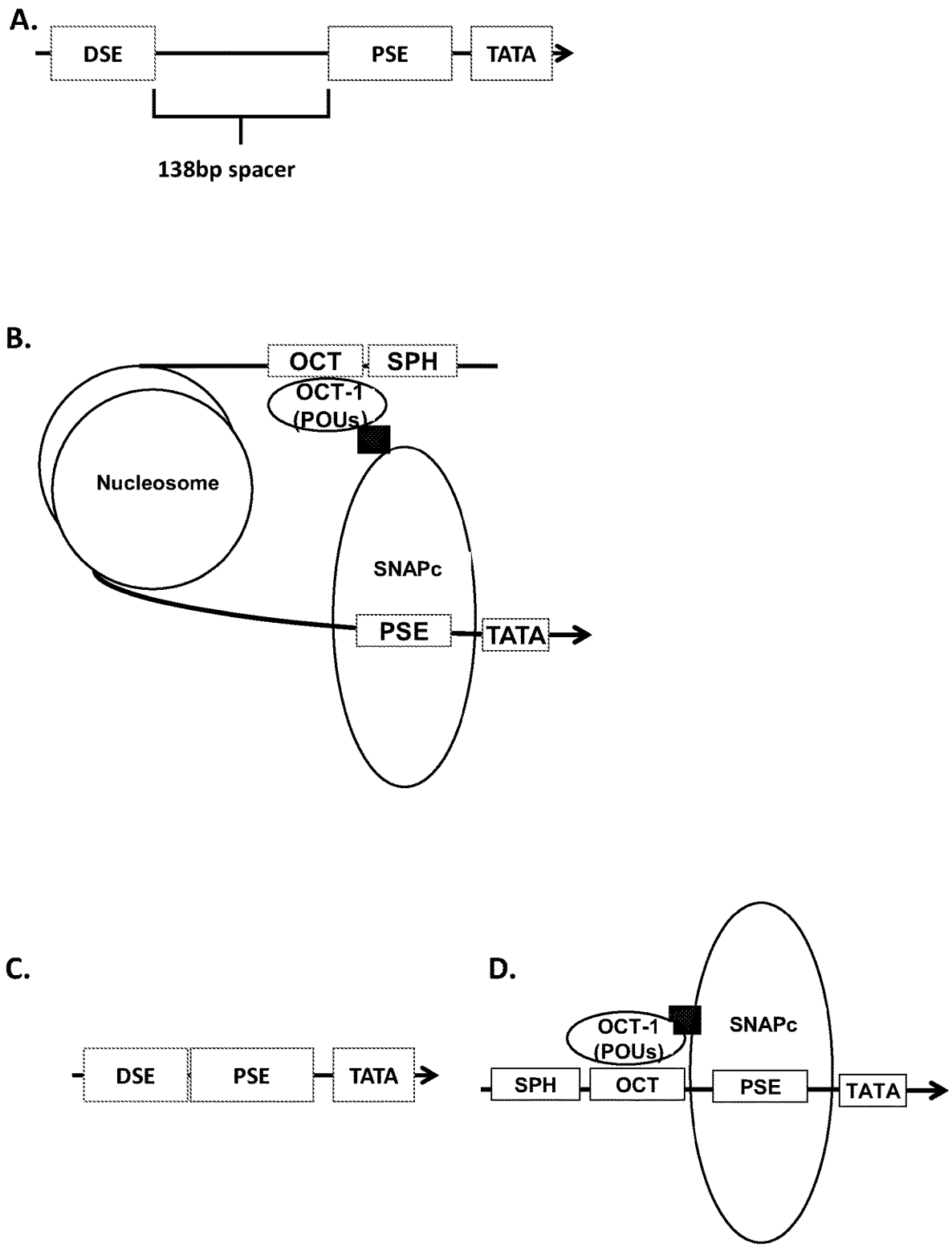
FIGS. 2—U6 promoter structure and function: A) DNA structure of the wild type U6 Pol III promoter. B) Functional model of U6 Pol III promoter described by Stunkel et al., 1997. In this model the spacer sequence is wrapped around a functional nucleosome that acts to bring transcription factors binding the OCT sequence which is in the DSE, into juxtaposition with the SNAP complex bound to the PSE. C) In the context of a lentiviral vector this spacer sequence is redundant. By removal of this sequence we generated a Minimal U6 promoter consisting of 111 bp (>50% capacity reduction from wild type). D) Proposed model of minimal U6 Pol III promoter function, where removal of functional nucleosome brings DSE and PSE into proximity, allowing protein-protein interactions between associated transcription factors.

SEQ ID NO: 1 provides the sequence of the wild-type human U6 promoter.

SEQ ID NO: 2 provides the sequence of the DSE of wild-type human U6 DSE.

SEQ ID NO: 3 provides the sequence of the SPH of wild-type human U6 DSE.

SEQ ID NO: 4 (atttgcat) provides the sequence of the OCT of wild-type human U6 DSE.

SEQ ID NO: 5 provides the spacer sequence connecting DSE to PSE in wild-type human U6 promoter.

SEQ ID NO: 6 provides the sequence of the PSE of wild-type human U6 promoter.

SEQ ID NO: 7 provides the spacer sequence connecting PSE to TATA box in wild-type human U6 promoter.

SEQ ID NO: 8 provides the sequence of the mini-U6 promoter of Example 5.

SEQ ID NO: 9 provides the sequence of the DSE of mini-U6 promoter of Example 5.

SEQ ID NO: 10 provides the sequence of the SPH of mini-U6 promoter of Example 5.

SEQ ID NO: 11 (atttgcat) provides the sequence of the OCT of mini-U6 promoter of Example 5.

SEQ ID NO: 12 (atacgatag) provides the sequence of the spacer sequence connecting DSE to PSE in mini-U6 promoter of Example 5.

SEQ ID NO: 13 provides the sequence of the PSE of mini-U6 promoter of Example 5.

SEQ ID NO: 14 provides the sequence of the spacer sequence connecting PSE to TATA box in mini-U6 promoter of Example 5.

SEQ ID NO: 15 provides the sequence of the wild-type human U6 promoter expressing CRISPR guide.

SEQ ID NO: 16 provides the sequence of the mini-U6 promoter of Example 5 expressing CRISPR guide RNA.

SEQ ID NO: 17 provides the sequence of the protospacer (TRAC) in the mini U6 promoter of Example 5.

SEQ ID NO: 18 provides the sequence of the cr1 scaffold.

SEQ ID NO: 19 provides the sequence of the cr2 scaffold.

SEQ ID NO: 20 provides the sequence of the cr3 scaffold.

SEQ ID NO: 21 provides the sequence 3' of the TATA box in the mini-U6 promoter of Example 5.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a molecule" includes "molecules", reference to "a T-cell" includes two or more such T-cells, reference to "a component" includes two or more such components, and the like.

All publications, patents and patent applications cited herein, whether supra or infra, are hereby incorporated by reference in their entirety.

Minimal U6 Pol III Promoter

The invention provides a U6 pol III promoter that is 74 bp to 117 bp in length and which comprises, from 5' to 3', a distal sequence element (DSE), a proximal sequence element (PSE) and a TATA box. This minimal U6 pol III promoter is much smaller in size than the wild-type U6 pol III promoter and can advantageously be used in a vector having a limited cargo capacity to allow a larger insert nucleic acid sequence to be used. This can be beneficial to achieving multiplexed effects.

The U6 pol III promoter is 74 bp to 117 bp in length. For example, the U6 pol III promoter may be 75 bp to 116 bp, 76 bp to 115 bp, 77 bp to 114 bp, 78 bp to 113 bp, 79 bp to 112 bp, 80 bp to 111 bp, 81 bp to 110 bp, 82 bp to 109 bp, 83 bp to 108 bp, 84 bp to 107 bp, 85 bp to 106 bp, 86 bp to 105 bp, 87 bp to 104 bp, 88 bp to 103 bp, 89 bp to 104 bp, 90 bp to 103 bp, 91 bp to 102 bp, 92 bp to 101 bp, 93 bp to 100 bp, 94 bp to 99 bp, or 95 bp to 98 bp in length. The U6 pol III promoter may for example be 75 bp to 115 bp, 80 bp to 110 bp, 85 bp to 105 bp, or 90 bp to 100 bp in length. The U6 pol III promoter may for example be up to 117 bp, up to 116 bp, up to 115 bp, up to 114 bp, up to 113 bp, up to 112 bp, up to 111 bp, up to 110 bp, up to 109 bp, up to 108 bp, up to 107 bp, up to 106 bp, up to 105 bp, up to 104 bp, up to 103 bp, up to 102 bp, up to 101 bp, up to 100 bp, up to 99 bp, up to 9 bp, up to 97 bp, up to 96 bp, up to 95 bp, up to 94 bp, up to 93 bp, up to 92 bp, up to 91 bp, up to 90 bp, up to 89 bp, up to 87 bp, up to 86 bp, up to 85 bp, up to 84 bp, up to 83 bp, up to 82 bp, up to 81 bp, up to 80 bp, up to 79 bp, up to 78 bp, up to 77 bp, up to 76 bp, or up to 75 bp in length. The U6 pol III promoter may for example be 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp or 117 bp in length.

As well as the DSE, PSE and TATA box, the U6 pol III promoter may comprise other DNA sequences. For example, the U6 pol III promoter may comprise a DNA sequence distal to (i.e. 5' of) the DSE. Alternatively, the most distal nucleotide of the DSE may form the most distal nucleotide of the U6 pol III promoter. The U6 pol III promoter may comprise a DNA sequence connecting the DSE to the PSE. The U6 pol III promoter may comprise a DNA sequence connecting the PSE to the TATA box. The U6 pol III promoter may comprise a DNA sequence proximal to (i.e. 3' of) the TATA box.

The DSE may be connected to the PSE by a DNA spacer sequence that is 9 bp or less in length. The DNA spacer sequence may be any DNA sequence that is 9 bp or less in length. For instance, the DNA spacer sequence may be 1 bp to 9 bp, 2 bp to 8 bp, 3 bp to 7 bp, or 4 bp to 6 bp in length. The DNA spacer sequence may be 1 bp, 2 bp, 3 bp, 4 bp, 5 bp, 6 bp, 7 bp, 8 bp or 9 bp in length. The DNA spacer sequence may, for example have the sequence of SEQ ID NO: 12.

The DSE may be connected to the PSE in the absence of an intervening DNA spacer sequence. In other words, the most proximal nucleotide of the DSE may be directly connected to the most distal nucleotide of the PSE.

The PSE may be connected to the TATA box by a DNA spacer sequence that is 40 bp or less in length. The DNA spacer sequence may be any DNA sequence that is 40 bp or less in length. For example, the PSE may be connected to the TATA box by a DNA spacer sequence that is 1 bp to 40 bp, 2 bp to 39 bp, 3 bp to 38 bp, 4 bp to 37 bp, 5 bp to 36 bp, 6 bp to 35 bp, 7 bp to 34 bp, 8 bp to 33 bp, 9 bp to 32 bp, 10 bp to 31 bp, 11 bp to 30 bp, 12 bp to 29 bp, 13 bp to 28 bp, 14 bp to 27 bp, 15 bp to 26 bp, 16 bp to 25 bp, 17 bp to 24 bp, 18 bp to 23 bp, 19 bp to 22 bp, to 20 bp to 21 bp in length. The PSE may be connected to the TATA box by a DNA spacer sequence that is, for example, 39 bp or less, 38 bp or less, 37 bp or less, 36 bp or less, 35 bp or less, 34 bp or less, 33 bp or less, 32 bp or less, 31 bp or less, 30 bp or less, 29 bp or less, 28 bp or less, 27 bp or less, 26 bp or less, 25 bp or less, 24 bp or less, 23 bp or less, 22 bp or less, 21 bp or less, 20 bp or less, 19 bp or less, 18 bp or less, 17 bp or less, 16 bp or less, 15 bp or less, 14 bp or less, 13 bp or les, 12 bp or less, 11 bp or less, 10 np or less, 9 bp or less 8 bp or less, 7 bp or less, 6 bp or less, 5 bp or less, 4 bp or less, 3 bp or less, 2 bp or less, or 1 bp or less in length. The DNA spacer sequence may be 0 bp in length. In other words, the most proximal nucleotide of the PSE may be directly connected to the most distal nucleotide of the TATA box. Preferably, the DNA spacer sequence connecting the PSE to the TATA box is 17 bp or less in length. The DNA spacer sequence may, for example have the sequence of SEQ ID NO: 14.

The U6 pol III promoter may comprise a DNA spacer sequence of 22 bp to 35 bp in length 3' of the TATA box. The DNA spacer sequence may be any DNA sequence that is 22 bp to 35 bp in length. The DNA spacer sequence 3' of the TATA box may, for example, be 23 bp to 34 bp, 24 bp to 33 bp, 25 bp to 32 bp, 26 bp to 31 bp, 27 bp to 30 bp, or 28 bp to 29 bp in length. Preferably, the DNA spacer sequence 3' of the TATA box is 22 bp to 25 bp in length. The DNA spacer sequence 3' of the TATA box may, for example, be 22 bp, 23 bp, 24 bp, 25 bp, 26 bp, 27 bp, 28 bp, 29 bp, 30 bp, 31 bp, 32 bp, 33 bp, 34 bp or 35 bp in length. The DNA spacer sequence 3' of the TATA box is preferably 25 bp in length. The DNA spacer sequence 3' of the TATA box may, for example, have the sequence of SEQ ID NO: 19.

The DSE may be 28 bp in length. The DSE may be identical to a DSE from a human U6 pol III promoter, for example a human U6 pol III promoter comprising the sequence of SEQ ID NO: 1. For instance, the DSE may comprise the sequence of SEQ ID NO: 2. The DSE may consist of the sequence of SEQ ID NO: 2.

The PSE may be 20 bp in length. The PSE may be identical to a PSE from a human U6 pol III promoter, for example a human U6 pol III promoter comprising the sequence of SEQ ID NO: 1. For instance, the PSE may comprise the sequence of SEQ ID NO: 6. The PSE may consist of the sequence of SEQ ID NO: 6.

The U6 pol III promoter may comprise the sequence of SEQ ID NO: 8. For example, the U6 pol III promoter U6 pol III promoter may consist of the sequence of SEQ ID NO: 8. Alternatively, the U6 pol III promoter may comprise a sequence that comprises from 5' to 3' the sequence of SEQ ID NO: 2, the sequence of SEQ ID NO: 6 and a TATA sequence, and that has at least 90% identity over its entire length to SEQ ID NO: 8. For example, the U6 pol III promoter may consist of a sequence that comprises from 5' to 3' the sequence of SEQ ID NO: 2, the sequence of SEQ ID NO: 6 and a TATA sequence, and that has at least 90% identity over its entire length to SEQ ID NO: 8. A sequence that has at least 90% identity over its entire length to SEQ ID NO: 8 may have, for example, at least 91%, at least 92%, at least 93%, at least 94%, at least 95%, at least 96%, at least 97%, at least 98%, at least 99%, or 100% identity over its entire length to SEQ ID NO: 8. A sequence that has at least 90% identity over its entire length to SEQ ID NO: 8 may have, for example, 90% to 95%, 95% to 100%, 90% to 100%, 91% to 99%, 92% to 98%, 93% to 97%, 94% to 96%, identity over is entire length to SEQ ID NO: 8.

Nucleic Acid Construct

The invention provides a nucleic acid construct comprising the minimal U6 pol III promoter described above. Preferably, the U6 pol III promoter is comprised in a 3' long terminal repeat region (LTR) of the nucleic acid construct.

The U6 pol III promoter may be operably linked to a sequence encoding a CRISPR guide sequence (sgRNA). The CRISPR guide sequence may be specific for any target. Preferably, the CRSPR guide sequence is suitable for disrupting expression of TCR and/or MHC class 1 in a T cell. Use of the minimal U6 pol III promoter for disrupting expression of TCR and/or MHC class 1 in a T cell is discussed in detail below.

The nucleic acid construct may comprise a cr1 scaffold sequence 3' of the U6 pol III promoter. The cr1 scaffold sequence is described in Gilbert et al. (2013). The cr1 scaffold sequence may comprise the sequence of SEQ ID NO: 18. The nucleic acid construct may comprise a cr2 scaffold sequence 3' of the U6 pol III promoter. The cr2 scaffold sequence is described in Adamson et al (2016). The cr2 scaffold sequence may comprise the sequence of SEQ ID NO: 19. The nucleic acid construct may comprise a cr3 scaffold sequence 3' of the U6 pol III promoter. The cr3 scaffold sequence is described in Adamson et al (2016). The cr2 scaffold sequence may comprise the sequence of SEQ ID NO: 20.

Vector

The present invention provides a vector comprising the nucleic acid construct described above.

Preferably, the vector may be a viral vector. Preferably, the viral vector is a lentivirus, a retrovirus, an adenovirus, an adeno-associated virus (AAV), a vaccinia virus or a herpes simplex virus. Methods for producing and purifying such vectors are known in the art. Preferably, the viral vector is a gamma-retrovirus or a lentivirus. The lentivirus may be a modified HIV virus suitable for use in delivering genes. The lentivirus may be a Simian Immunodeficiency Virus (SIV), Feline Immunodeficiency Virus (FIV), or equine infectious anemia virus (EQIA) based vector. The viral vector may comprise a targeting molecule to ensure efficient transduction with the nucleic acid sequence or nucleic acid construct. The targeting molecule will typically be provided wholly or partly on the surface of the viral vector in order for the molecule to be able to target the virus to T-cells. The viral vector is preferably replication deficient.

The vector may be a non-viral vector. Preferably, the non-viral vector is a DNA plasmid, a naked nucleic acid, a nucleic acid complexed with a delivery vehicle, or an artificial virion. The non-viral vector may be a human artificial chromosome. When the non-viral vector is a nucleic acid complexed with a delivery vehicle, the delivery vehicle may be a liposome, virosome, or immunoliposome. Integration of a plasmid vector may be facilitated by a transposase such as sleeping beauty or PiggyBAC.

Method for Delivering CRISPR Guide Sequences and a CRISPR Guided DNA Modification Enzyme Gene editing approaches based on Zinc Finger Nucleases and TALENs have recently reached clinical phase applications, with T cells the first ex vivo engineered cells to be applied in man. Efficiency of editing has been modest, with delivery of mRNA encoding nuclease reagents by electroporation. Emerging CRISPR/Cas9 reagents are opening new possibilities of genome editing, but a key hurdle remains efficient delivery in primary human cells. In particular, one limitation is the ability to scale the RNA or protein delivery.

Lentiviral mediated delivery of CRISPR guide sequences and Cas9 CRISPR nuclease has been reported. Such vectors integrate and stably express target specific guide RNA using pol III promoter elements, and separately express Cas9 protein under the control of internal mammalian/viral promoter elements for gene editing effects. These lentiviral vectors are suitable for experimental purposes in a research setting, but stable expression of Cas9 would be problematic for therapeutic use. There would be ongoing Cas9 complexing with CRISPR RNA, resulting in further DNA scission effects, possibly including off-target activity. In addition Cas9 is of bacterial origin and could trigger immunogenic responses.

The "terminal CRISPR" technique described in WO 2018/115887 addresses the problems associated with the traditional lentiviral mediated delivery of CRISPR guide sequences and Cas9 CRISPR nuclease. Terminal CRISPR is an integrating self-inactivating vector, designed to deliver and stably express therapeutic transgene(s) (such as chimeric antigen receptors (CARs), rTCR, suicide gene, antiviral restriction factor, recombinant coding DNA for inherited gene defects, or an FcR) under the control of an internal human promoter and to simultaneously mediate highly specific DNA scission through expression of CRISPR guide nucleic acids. The guide nucleic acids act in concert with a CRISPR guided DNA modification enzyme delivered separately to the target cell, for instance by mRNA electroporation. The CRISPR guide sequences and associated promoters are incorporated into a 3' terminal repeat (LTR) sequence of the vector plasmid, and are thereby duplicated during reverse transcription. For instance, if the CRISPR guide sequences are incorporated in the 3'LTR, they are copied to the 5'LTR during reverse transcription.

The configuration of the terminal CRISPR vector has a number of advantages:
  i. Avoiding promoter interference during vector genome expression during vector manufacture or with transgene expression, thereby retaining titre and expression comparable to conventional vectors;
  ii. Doubling guide RNA expression through duplication effects; and
  iii. Linking and thereby restricting guide effects to cells transduced with vector and expressing transgene.
  iv. Linking transgene expression to guide effects, thereby facilitating purification and enrichment of transduced cells.

Furthermore, in contrast with more traditional genome editing techniques, such as ZFNs or TALENs, the CRISPR approach in general has several further advantages:
  i. A greater number of gene loci can be targeted than with TALENs, ZFNs, Mega-talens or meganucleases;
  ii. Multiplex effects can be more easily secured; and
  iii. Greatly reduced cost of manufacture of vector plus a single batch of Cas9 mRNA compared to multiple (pairs) of targeting nuclease reagents.

CRISPR/Cas9 gene disruption is conventionally mediated by DNA double-strand breaks (DSBs). CRISPR base editing inactivates genes by converting four codons CAA, CAG, CGA, and TGG into STOP codons (Billon et al, Molecular Cell, Volume 67, Issue 6, 21 Sep. 2017, Pages 1068-1079; Kuscu et al Nature Methods 14, 710-712 2017), or by disruption of splice sites (Zhenxiang et al, New Phytologist, Epub 18 Dec. 2018). CRISPR base editing has the advantage of not causing DSBs, and thus reduces the risk of translocations. This is especially true in the multiplex setting. CRISPR guides can be designed to specifically target a splice acceptor/donor consensus sequences at an exon termini.

To arrive at the terminal CRISPR platform, expression of a CRISPR guided DNA modification enzyme has been divorced from the vector delivering the CRISPR guide sequences. Instead, a CRISPR guided DNA modification enzyme is delivered separately to the target cell. For instance, a CRISPR guided DNA modification enzyme may be provided as CRISPR nuclease mRNA and delivered by electroporation. A CRISPR guided DNA modification enzyme may be provided as a protein. Separate delivery of a CRISPR guided DNA modification enzyme allows the CRISPR guided DNA modification enzyme to be expressed transiently and to have time-limited effects, as it becomes diluted in rapidly dividing cells. A CRISPR guided DNA modification enzyme provided transiently is also less likely to be immunogenic.

Appropriate CRISPR guided DNA modification enzyme are known in the art. The guided DNA modification enzyme may be a CRISPR nuclease. The CRISPR nuclease may be Cas. Preferably, the CRISPR nuclease is Cas9. The Cas9 may be *Streptococcus pyogenes* Cas9 (SpCas9) or *Staphylococcus aureus* Cas9 (SaCas9). CRISPR nucleases from any bacteria may though be used. Dead Cas or nickases could also be used, to give rise to effects such as repression or cytidine deamination. The CRISPR guided DNA modification enzyme may be a cytidine deaminase. The CRISPR guided DNA modification enzyme may be repressor or activator CRISPR guided DNA modification enzyme.

In terminal CRISPR, expression of CRISPR guide sequences is mediated by promoters contained in a 3'long terminal repeat region (LTR) present in the vector. During reverse transcription, the LTR region is duplicated and becomes incorporated into both the 5' and 3' LTR, resulting in two expression cassettes. Thus, guide sequence expression is increased, and the likelihood of and interference effect between CRISPR guide sequences and any transgene additionally encoded in the vector is reduced.

Terminal CRISPR vectors that also encode a transgene, such as a CAR, have been found to be highly effective, with numerous beneficial effects. In particular:
  No significant reduction in vector titre or transgene expression as a result of additions to the LTRs in the terminal CRISPR vectors has been observed. This means that the invention is readily translatable to large scale applications.
  The Terminal-CRISPR approach removes the cost of bespoke mRNA production, and only requires a single stock of Cas9 mRNA. There are already platforms aiming to gene edit CAR expressing T cells, including TALENs, that are in clinical phase evaluation. These platforms rely on mRNA delivery of two specific TALEN pairs for each locus targeted, adding notably to the cost of each manipulation. This cost is avoided with the terminal CRISPR approach.
  The ability to include CRISPR guide sequences in the vector that also encodes a transgene, such as CAR or a FcR, ensures that knock out effects can only occur in transduced cells. This improves safety and reduces the risk of unwanted effects
  LTR duplication results is replication of CRISPR sequences, and thereby supports enhanced expression.

The invention provides a method for delivering CRISPR guide sequences and a CRISPR guided DNA modification enzyme to a cell, comprising (a) introducing one or more CRISPR guide sequences to said cell using a nucleic acid construct that comprises a 3' LTR comprising a U6 pol III promoter the invention operably linked to a sequence encoding said CRISPR guide sequence(s); and (b) separately delivering the CRISPR guided DNA modification enzyme to said cell of (a) by introducing into it a nucleic acid or protein sequence encoding said CRISPR guided DNA modification enzyme.

The nucleic acid construct may be comprised in a vector. The vector may be a viral vector. Viral vectors are discussed in detail above. The vector may be a lentiviral vector. The vector may be a 3rd generation lentiviral vector. The vector may be a gamma retroviral vectors and an alpha retroviral vector.

The 3' LTR of the nucleic acid construct comprises a U6 pol III promoter the invention. The LTR may comprise a H1 promoter. The LTR may comprise a further U6 promoter. The LTR may comprise two or more different promoter sequences. For example, the LTR may comprise a H1 promoter sequence and a U6 promoter sequence, and optionally one or more other different promoter sequences. Each promoter (H1, U6 or otherwise) may be operably linked to a sequence encoding one CRISPR guide sequence.

The LTR may comprise several different promoters each operably linked to a sequence encoding one CRISPR guide sequence. In other words, the LTR may comprise two or more sequences encoding a CRISPR guide sequence each operably linked to a different promoter sequence. The promoter sequence to which each of the two or more sequences is operably linked is a different type of promoter sequence. For instance, a first sequence encoding a CRISPR guide sequence may be operably linked to a U6 promoter sequence, while a second sequence encoding a CRISPR guide sequence may be operably linked to a H1 promoter sequence. The H1 promoter sequence may be a full length or minimal H1 Pol III promoter sequence.

When the LTR comprises several promoters each operably linked to a sequence encoding one CRISPR guide sequence, the CRISPR guide sequences encoded by the sequences operably linked to each promoter may be the same or different. That is, when the LTR comprises two or more sequences encoding a CRISPR guide sequence each operably linked to a promoter sequence, the CRISPR guide sequences encoded by each of the two sequences may be the same or different. Preferably, the sequences are different. If the CRISPR guide sequences are different, they may target the same locus or different loci. Targeting different loci allows the expression of two or more different target molecules to be disrupted using the same terminal CRISPR vector, i.e. the terminal CRISPR approach can be "multiplexed". Any combination of target molecules may be targeted in this way using a single terminal CRISPR vector. For instance, a single terminal CRISPR vector may be use to target (i) TRAC and CD52, (ii) TRAC and PD1, (iii) PD1 and β2M, (iv) TRAC and CD123, (v) TRAC and CD52, (vi) TRAC and TRBC1, or (vii) TRAC and TRBC2. Operably linking each sequence encoding a different CRISPR guide sequence to a different promoter sequence prevents recombination effects, allowing each guide sequence to be efficiently expressed.

Following delivery of the vector, the promoter sequence(s) may be duplicated during reverse transcription such that it becomes incorporated into both the 5' and 3' LTRs. Likewise, the guide sequence(s) may be duplicated during reverse transcription such that it becomes incorporated into both the 5' and 3' LTRs.

The nucleic acid sequence encoding the CRISPR guided DNA modification enzyme may be RNA, such as mRNA. The nucleic acid sequence encoding the CRISPR guided DNA modification enzyme may be DNA.

The nucleic acid construct may further comprise a sequence encoding a CAR. The CAR may be specific for, CD2, CD7, CD10, CD19, CD20, CD22, CD30 CD33, CD123, CD45 erb-B2, CEA, IL13R, Ror, kappa light chain, TCR-beta constant 1, TCR-beta constant 2, MAGE-A1, MUC1, PSMA, VEGF-R, Her2, or CAIX. The CAR may be specific for CD19. The vector may further comprise a sequence encoding a FcR.

One or more of the CRISPR guide sequences may be specific for the TRAC locus. One or more of the CRISPR guide sequences may be specific for the TAP1 locus. One or more of the CRISPR guide sequences may be specific for the TAP2, Beta-2 microglobulin ($β_2m$), CIITA, RFX5, RFXAP or RFXANK locus. One or more of the CRISPR guide sequences may be specific for a locus controlling a checkpoint inhibitor pathway. One or more of the CRISPR guide sequences is specific for the locus controlling expression of CD52. One or more of the CRISPR guide sequences is specific for a locus controlling the expression of an antigen targeted by a CAR, chimeric FcR or monoclonal antibody expressed by the cells.

In one aspect, the nucleic acid construct comprises a sequence encoding a CAR specific for CD19, and one or more CRISPR guide sequences specific for a locus controlling the expression of the TCR-CD3 complex. The nucleic acid construct may comprise a sequence encoding a CAR specific for CD19, and one or more CRISPR guide sequences specific for the TRAC locus.

This terminal CRISPR method for delivering CRISPR guide sequence and CRISPR guided DNA modification enzyme to a cell may be used to disrupt the expression of TCR and/or MHC class I in T cells. For TCR disruption, the guide sequence(s) may be specific for the TRAC locus, a TCR beta constant locus or CD3 locus. For MHC class I disruption, the guide sequence(s) may be specific for the TAP1, TAP2 or $β_2m$. For MHC class II disruption, the guide sequence(s) may be specific for the CIITA, RFX5, RFXAP or RFXANK locus. The terminal CRISPR method may be used in the generation of universal antibody dependent cord T cells (U-ACTs). In this case, the nucleic acid sequence encoding the FcR and the CRISPR guide sequence(s) may be introduced to the cord blood T cells in the same vector. The terminal CRISPR method may be used in the generation of TCR-CAR19+ T cells. In this case, the nucleic acid sequence encoding the CAR specific for CD19 and the CRISPR guide sequence(s) specific for a locus controlling the expression of the TCR-CD3 complex may be introduced to the T cells in the same vector. Delivery in the same vector is associated with the advantages set out above.

The terminal CRISPR method for delivering CRISPR guide sequence and CRISPR guided DNA modification enzyme to a cell further has almost limitless applications in cell engineering. Terminal CRISPR may be used to modify any type of cell or therapeutic cell. For instance, terminal CRISPR may be used in a cord blood T cell, a peripheral blood lymphocyte, a hematopoietic stem cell, a mesenchymal stem cell, a fibroblast, or a keratinocyte. The cell modified using terminal CRISPR may be autologous or allogeneic to an individual into which the cell is to be administered. Terminal CRISPR may be used to disrupt the expression of any gene expressed in any cell type. The terminal CRISPR vector may be used to introduce any transgene into the any cell. Exemplary uses of terminal CRISPR are as follows.

Terminal CRISPR may be used to modify a cord blood T cell. When terminal CRISPR is used to modify a cord blood T cell, it may be used disrupt expression of TCR and/or MHC class I. Concurrently, the terminal CRISPR may be used to introduce a FcR and/or a CAR. For instance, terminal CRISPR may be used to (i) disrupt expression of TCR and MHC class I and introduce a FcR; (ii) disrupt expression of TCR and MHC class I and introduce a CAR, such as a CAR specific for CD2, CD7, CD10, CD19, CD20, CD22, CD33, CD123 or CD3; or (iii) disrupt expression of TCR or MHC1 and introduce a CAR specific for CD3.

Likewise, terminal CRISPR may be used to modify an allogeneic peripheral blood lymphocyte (PBL), such as a T cell or a B cell. When terminal CRISPR is used to modify an allogeneic PBL, it may be used disrupt expression of TCR and/or MHC class I. Concurrently, the terminal CRISPR may be used to introduce a FcR and/or a CAR. For instance, terminal CRISPR may be used to (i) disrupt expression of TCR and MHC class I and introduce a FcR such as the FcR of the invention; (ii) disrupt expression of TCR and MHC class I and introduce a CAR, such as a CAR specific for CD2, CD7, CD10, CD19, CD20, CD22, CD33, CD123 or CD3; or (iii) disrupt expression of TCR or MHC1 and introduce a CAR specific for CD3.

Terminal CRISPR may also be used to modify an autologous cell, such as an autologous PBL or hematopoietic stem cell (HSC). Using terminal CRISPR, and autologous PBL or HSC may be modified in several key ways:
  i. disruption of TCR and/or CD3 expression and introduction of arTCR. This approach leads to enhanced expression of rTCR through removal of competition for CD3, and prevention of cross pairing, reducing the risk of autoreactive TCRs.
  ii. disruption of a viral co-receptor and introduction of an anti-viral factor such as a restriction factor. For instance, expression of CCR5 (an HIV co-receptor) may be disrupted. The restriction factor TRIM5CypA, C46 HIV fusion inhibitor, TRIM21, CylcophilinA, APOBEC, SAMHD1 or Tetherin may be targeted.
  iii. disruption of gain-of function mutations and introduction of replacement cDNA. This therapeutic approach allows a two-prong attack using a single vector. Gain of function mutations include mutations in genes such as STAT1, STAT3, NFKB1A, CARD11, CXCR4 and PI3K.
  iv. disruption of transgene-silencing pathways and introduction of a protein lacking or mutated cell. This gene therapy approach release inhibition on transgene expression, allowing sustained, longer term expression of replacement protein. Human silencing Hub (HUSH) complex pathways, or TASOR (transgene activator suppressor) protein may be targeted. MMP8 or Periphilin may be targeted.
  v. disruption of checkpoint inhibitor pathways (e.g. PD-1) and introduction of a suicide gene. Disruption of checkpoint inhibitor pathways unleashes an immune system attack on cancer cells. Introduction of a suicide gene provides an "off switch" for the disinhibited cells. Any suitable suicide gene may be used. Suicide genes are well-known in the art and include Herpes simplex virus thymidine kinase and mutated variants, inducible caspases and cell surface proteins incorporating epitope targets for antibodies against CD20 or EGFR.

It can therefore be appreciated that the potential utility of the terminal CRISPR approach is very broad. Accordingly, the invention further provides use of a nucleic acid construct that comprises a 3' LTR comprising a U6 pol III promoter of the invention operably linked to a sequence encoding a CRISPR guide sequence to:
  (a) disrupt expression of TCR and/or MHC class 1 in a cell;
  (b) introduce a nucleic acid sequence encoding a FcR that comprises (I) an extracellular domain that is capable of binding to a constant domain of an antibody and (II) a transmembrane domain and a cytoplasmic domain that are capable of supporting T cell activation into a cell;
  (c) introduce a nucleic acid sequence encoding a CAR into a cell, optionally wherein the CAR is specific for, CD2, CD7, CD10, CD19, CD20, CD22, CD30, CD33, CD45, CD123, erb-B2, CEA, IL13R, Ror, kappa light chain, TCR-beta constant 1, TCR-beta constant 2, MAGE-A1, MUC1, PSMA, VEGF-R, Her2, or CAIX;
  (d) introduce a nucleic acid sequence encoding a CAR into a cell and to disrupt expression of TCR and/or MHC class 1 in the cell, optionally wherein the CAR is specific for CD2, CD7, CD10, CD19, CD20, CD22, CD30, CD33, CD45, CD123, erb-B2, CEA, IL13R, Ror, kappa light chain, TCR-beta constant 1, TCR-beta constant 2, MAGE-A1, MUC1, PSMA, VEGF-R, Her2, or CAIX;
  (e) introduce a nucleic acid sequence encoding a rTCR into a cell and to disrupt expression of TCR in the cell;
  (f) introduce a nucleic acid sequence encoding a restriction factor into a cell and to disrupt expression of CCR5 in the cell, optionally wherein the restriction factor is TRIM5CypA;
  (g) disrupt expression of a locus controlling a gain of function mutation in a cell and to introduce a nucleic acid sequence encoding a replacement protein into the cell;
  (h) disrupt expression of a locus controlling a transgene silencing pathway in a cell, optionally wherein the vector comprises a nucleic acid sequence encoding a transgene silenced by the pathway; or
  (i) disrupt expression of a locus controlling a checkpoint inhibitor pathway in a cell and to introduce a nucleic acid sequence encoding a suicide into the cell.

Any of the aspects described above in connection with the minimal U6 pol III promoter, nucleic acid construct or vector of the invention may apply equally to the method for delivering CRISPR guide sequences and a CRISPR guided DNA modification enzyme to a cell, or use of a nucleic acid construct that comprises a 3' LTR comprising a U6 pol III promoter of the invention operably linked to a sequence encoding a CRISPR guide sequence.

Generation of TCR-CAR+ T Cells and MHC Class 1-CAR+ T Cells

The invention provides a method for generating T cells that comprise a nucleic acid sequence encoding a CAR and have disrupted TCR and/or MHC class 1 expression, comprising: (a) providing one or more T cells; (b) introducing into one or more of said T cells of (a) a nucleic acid sequence encoding a CAR; and (c) disrupting expression of TCR and/or MHC class 1 in said T cells of (b), wherein, in (c), the expression of TCR and/or MHC class 1 is disrupted by: (i) introducing one or more CRISPR guide sequences to said T cells of (b) using a nucleic acid construct that comprises a 3' LTR comprising a U6 pol III promoter of the invention operably linked to a sequence encoding said CRISPR guide sequence(s); and (ii) separately delivering a CRISPR guided DNA modification enzyme to said T cells of (b) by introducing into them a nucleic acid or protein sequence encoding said CRISPR guided DNA modification enzyme.

The CAR may be specific for any antigen, such as CD2, CD7, CD10, CD19, CD20, CD22, CD30, CD33, CD45, CD123, erb-B2, CEA, IL13R, Ror, kappa light chain, TCR-beta constant 1, TCR-beta constant 2, MAGE-A1, MUC1, PSMA, VEGF-R, Her2, or CAIX. For example, the CAR may be specific for CD19 (i.e. in TCR-CAR19+ T cells), CD20 (i.e. in TCR-CAR20+ T cells), CD22 (i.e. in TCR-CAR20+ T cells) or CD123 (i.e. in TCR-CAR123+ T cells).

The T cells of (a) may comprise CD8+ T cells, or cytotoxic T cells. The T cells may comprise CD4+ T cells, or helper T cell ($T_H$ cells), such as a $T_H1$, $T_H2$, $T_H3$, $T_H17$, $T_H9$, or $T_{FH}$ cells. The T cells may comprise regulatory T cells (Treg).

The T cells may be stimulated after separation prior to use in (a), for example after separation from a sample of cord blood. For instance, the T cells may be contacted with an anti-CD3 antibody and/or an anti-CD28 antibody. In this way, the T cells may be activated or expanded. The anti-CD3 antibody and/or the anti-CD28 antibody may be present on microbeads. The anti-CD3 antibody and/or the anti-CD28 antibody may be used in combination with cytokines such as interleukin-2, interleukin-7 and interleukin-15, alone or in combination.

Once T cells are provided, a nucleic acid sequence encoding a chimeric antigen receptor (CAR) is introduced into one or more of the T cells. CARs are engineered receptors, which graft a selected specificity onto an immune effector cell. CARs usually incorporate a single chain variable fragment (scfv) derived from the antigen binding regions of an antibody, linked to an intracellular activation domain. Thus, the CAR may comprise an ectodomain capable of binding to an antigen and a transmembrane domain and a cytoplasmic domain that are capable of supporting T cell activation. The ectodomain may comprise an antibody, a monoclonal antibody, or a scfv specific for CD19, for instance. The ectodomain may be specific for CD2, CD7, CD10, CD19, CD20, CD22, CD30, CD33, CD45, CD123, erb-B2, CEA, IL13R, Ror, kappa light chain, TCR-beta constant 1, TCR-beta constant 2, MAGE-A1, MUC1, PSMA, VEGF-R, Her2, or CAIX. The ectodomain may be specific for CD19, CD20 or CD22. The cytoplasmic domain may comprise one or more of CD3ζ, OX40, CD28 and 4-1BB cytoplasmic domains.

The cytoplasmic domain of the CAR may comprise an activation domain. The activation domain serves to activate the T cell following engagement of the extracellular domain. For instance, the cytoplasmic domain may comprise one or more of a 41BB activation domain, a CD3ζ activation domain and a CD3e activation domain. Preferably, the cytoplasmic domain comprises a 41BB activation domain and/or a CD3ζ activation domain.

The nucleic acid sequence encoding the CAR may be introduced to the T cells using any method known in the art. In particular, the T cells may be transfected or transduced with the nucleic acid sequence.

The nucleic acid sequence transduced or transfected into the T cells gives rise to expression of CAR in the T cells. Preferably, the nucleic acid sequence is transduced into the T cell. In this case, the vector used for transduction may comprise a further nucleic acid sequence encoding another molecule useful to the generation of TCR-CAR+ T cells or MHC1-CAR+ T cells. In particular, CRISPR guide sequences targeting a gene associated with expression of the TCR-CD3 complex and/or a gene associated with the expression of MHC class 1 may be present in the same vector as the nucleic acid sequence encoding the CAR.

To make the TCR-CAR+ T cells more universal by reducing the capability of the cells to cause GVHD in an individual to which they are administered, their expression of TCR is disrupted. MHC expression may also be disrupted, in particular MHC class I. Mechanisms known in the art for disrupting these molecules include genome editing using zinc finger nucleases (ZFNs), Meganucleases, transcription activator-like effector nucleases (TALENs), or the clustered regularly interspaced short palindromic repeats (CRISPR)/ Cas system. All of these genome editing methods can disrupt a gene, entirely knocking out all of its output.

The terminal CRISPR approach described above is used to disrupt expression of TCR and/or MHC class 1. For instance, terminal CRISPR may be used to disrupt expression of TCR. Terminal CRISPR may be used to disrupt expression of MHC class 1. Terminal CRISPR may be used to disrupt expression of TCR and MHC class 1. Terminal CRISPR may be used to disrupt expression of TCR, and ZFNs, TALENS or CRISPR may be used to disrupt expression of MHC class 1. Terminal CRISPR may be used to disrupt expression of MHC class 1, and ZFNs, TALENS or CRISPR may be used to disrupt expression of TCR.

Irrespective of the method used to disrupt TCR expression, TCR expression may be disrupted by targeting one or more of the T cell receptor alpha constant (TRAC) locus, TCR beta constant locus, or CD3 receptor complex chains. The TCR beta constant locus may be C1 or C2. Preferably, the TRAC locus is targeted.

If terminal CRISPR is used to disrupt TRAC expression in the formation of TCR-CAR+ T cells, the resultant TCR-CAR+ T cells may be referred to as terminal TRAC TCR-CAR+ T cells (TT TCR-CAR+ T cells, e.g. TT TCR-CAR19+ T cells).

Likewise, MHC class 1 may be disrupted by targeting the transporter associated with antigen processing (TAP1 or TAP2) locus, whichever method of disruption is used. The TAP1 locus may be targeted. MHC class 1 may be disrupted by Beta-2 microglobulin ($\beta_2$m) locus, whichever method of disruption is used. Preferably, the $\beta_2$m locus is targeted. MHC class II molecules may also be disrupted by targeting transcription factors controlling MHC expression such as CIITA, RFX5, RFXAP or RFXANK.

Any of the aspects described above in connection with the minimal U6 pol III promoter, nucleic acid construct or vector of the invention may apply equally to the method for generating T cells that comprise a nucleic acid sequence encoding a CAR and have disrupted TCR and/or MHC class 1 expression.

Generation of U-ACTs

The invention provides method for generating universal antibody dependent cord T cells (U-ACTs), comprising: (a) providing a sample of cord blood; (b) separating cells that express CD62L from the sample, wherein the cells that express CD62L comprise cord blood T cells; (c) introducing into one or more of said cord blood T cells of (b) a nucleic acid sequence encoding an Fc-Receptor (FcR) that comprises (I) an extracellular domain that is capable of binding to a constant domain of an antibody and (II) a transmembrane domain and a cytoplasmic domain that are capable of supporting T cell activation; and (d) disrupting expression of T cell receptor and MHC class I in said cord blood T cells of (c), wherein, in (d), the expression of T cell receptor and/or MHC class 1 is disrupted by: (i) introducing one or more CRISPR guide sequences to said cord blood T cells of (c) using a nucleic acid construct that comprises a 3' LTR comprising a U6 pol III promoter of any one of claims 1 to 15 operably linked to a sequence encoding said CRISPR guide sequence(s); and (ii) separately delivering a CRISPR guided DNA modification enzyme to said cord blood T cells of (c) by introducing into them a nucleic acid or protein sequence encoding said CRISPR guided DNA modification enzyme.

According to the method of the invention, U-ACTs are generated from cord blood T cells. The use of cord blood T cells is advantageous because they have a naïve phenotype, an immense proliferative potential and potent in vivo activity in transplant recipients. Thus, the method described herein begins with a sample of cord blood. The sample of cord blood may be any type of sample. For instance, the sample of cord blood may be fresh cord blood or frozen cord blood. The sample of cord blood may have been derived from one individual. The sample of cord blood may have been derived from multiple individuals, i.e. a pooled cord blood sample.

Cord blood T cells are obtained from the cord blood sample by separating cells that express CD62L from the sample. Any appropriate method may be used to separate cells that express CD62L from the sample. For instance, the cells that express CD62L may be separated from the sample based on their ability to bind an anti-CD62L antibody. The anti-CD62L antibody may be 145/15 (Miltenyi), DREG-56 (Biolegend, BD), FMC46 (BioRad) or LAM-116 (Merck). Fluorescence activated cell sorting (FACS) or magnetic activated cell sorting (MACS) may be used to separate the cells that express CD62L from the sample. In MACS, magnetic beads are conjugated to the anti-CD62L antibody. Binding of the CD62L-expressing cells to the anti-CD62L antibody therefore tags the cells with magnetic beads. Magnetism can therefore be used to separate the tagged cells from the sample.

The separation step may be manually performed. Alternatively, the separation step may be performed in a system designed for the automated separation of cells. In one aspect, the system is configured for automated production of cord T cells. The system may be a CliniMacs system or a Miltenyi Prodigy system. Other automated cell separation systems are known in the art.

The CD62L-expressing cells separated from the sample comprise cord blood T cells. Thus, the CD62L-expressing cells may comprise CD8+ T cells, or cytotoxic T cells. The CD62L-expressing cells may comprise CD4+ T cells, or helper T cell ($T_H$ cells), such as a $T_H1$, $T_H2$, $T_H3$, $T_H17$, $T_H9$, or $T_{FH}$ cells. The CD62L-expressing cells may comprise regulatory T cells (Treg).

In some aspects, the CD62L-expressing cells comprising cord blood T cells are stimulated after separation from the sample of cord blood. For instance, the CD62L-expressing cells may be contacted with an anti-CD3 antibody and/or an anti-CD28 antibody. In this way, the cord blood T cells may be activated or expanded. This can further increase the proportion of cord blood T cells among the selected CD62L-expressing cells. The anti-CD3 antibody and/or the anti-CD28 antibody may be present on microbeads.

Once cord blood T cells are obtained, a nucleic acid sequence that encodes an Fc-Receptor (FcR) is introduced into one or more of the cord blood T cells. An FcR is a protein that is endogenously found on the surface of certain immune cells, such as B lymphocytes, follicular dendritic cells, natural killer cells, macrophages, neutrophils, eosinophils, basophils, human platelets, and mast cells. FcRs are named for their ability to bind to part of an antibody constant region known as the Fc (Fragment, crystallizable) region. FcRs can bind to antibodies that are attached to diseased cells or invading pathogens, stimulating phagocytic or cytotoxic cells to destroy microbes or diseased cells by antibody-mediated phagocytosis or antibody-dependent cell-mediated cytotoxicity respectively.

The FcR comprises (I) an extracellular domain that is capable of binding to a constant domain of an antibody and (II) a transmembrane domain and a cytoplasmic domain that are capable of supporting T cell activation. The FcR may comprise a CD8 transmembrane domain "stalk" and 4-1BB and CD3ζ cytoplasmic domains. The extracellular domain may comprise a domain derived from antibody light chain. In this case, the FcR has improved dimerization ability, and therefore improved clustering.

The extracellular domain may comprise an extracellular domain of a variant FcRIIIA. FcRIIIA is also known as CD16. CD16 is a low affinity FcR, naturally found on the surface of natural killer cells, neutrophil polymorphonuclear leukocytes, monocytes and macrophages.

The antibody whose constant domain is bound by the extracellular domain may be an IgG antibody, such as an IgG1 antibody. The antibody may be a monoclonal antibody or a polyclonal antibody. The antibody may be a therapeutic antibody. The antibody may be a human antibody. The antibody may be a humanised antibody. The antibody may be a non-human antibody, such a, canine, equine, bovine, ovine, porcine, murine, feline, leporine, cavine or camelid antibody, having human IgG constant domains. Preferably, the antibody is a therapeutic monoclonal human antibody, or a therapeutic monoclonal humanised antibody.

The antibody may be specific for a marker expressed on a particular type of cells. For instance, the antibody may be specific for a B cell marker, such as CD20. CD20 is an activated-glycosylated phosphoprotein expressed on the surface of all B-cells beginning at the pro-B phase (CD45R+, CD117+) and progressively increasing in concentration until maturity. Preferably, the CD20-specific antibody is Rituximab. Rituximab destroys B cells and is therefore used to treat diseases which are characterized by overactive, dysfunctional, or excessive numbers of B cells. This includes many lymphomas, leukemias, transplant rejection, and autoimmune disorders. The antibody may be Ofatumumab. Ofatumumab may be used to treat chronic lymphocytic leukemia, Follicular non-Hodgkin's lymphoma, Diffuse large B cell lymphoma, rheumatoid arthritis and relapsing remitting multiple sclerosis.

The antibody may be specific for CD22. CD22 is found on the surface of mature B cells and to a lesser extent on some immature B cells. Generally speaking, CD22 is a regulatory molecule that prevents the overactivation of the immune system and the development of autoimmune diseases. Preferably, the CD22-specific antibody is Inotuzumab. Inotuzumab is an anti-cancer drug which may be used to treat non-Hodgkin lymphoma and acute lymphoblastic leukemia.

The antibody may be specific for CD38. CD38 is a glycoprotein found on the surface of many immune cells, including CD4+, CD8+, B lymphocytes and natural killer cells. CD38 also functions in cell adhesion, signal transduction and calcium signaling. Preferably, the CD38-specific antibody is Daratumumab. Daratumumab is an anti-cancer drug targeting multiple myeloma.

The antibody may be specific for CD52. CD52 is a glycoprotein present on the surface of mature lymphocytes, but not on the stem cells from which these lymphocytes were derived. It also is found on monocytes and dendritic cells. Preferably, the CD52-specific antibody is Alemtuzumab. Alemtuzumab is a drug used in the treatment of chronic lymphocytic leukemia (CLL), cutaneous T-cell lymphoma (CTCL), T-cell lymphoma and multiple sclerosis.

The antibody may be specific for EGFR. EGFR is the cell-surface receptor for members of the epidermal growth factor family (EGF family) of extracellular protein ligands. Preferably, the EGFR-specific antibody is Panitumumab. Panitumumab is a drug used in the treatment of colorectal cancer.

The antibody may be specific for Erb2. Erb2 is otherwise known as HER2. HER2 is a member of the human epidermal growth factor receptor (HER/EGFR/ERBB) family. Amplification or over-expression of this oncogene has been shown to play an important role in the development and progression of certain aggressive types of breast cancer. Preferably, the HER2-specific antibody is Herceptin (Trastuzumab) or Pertuzumab. Pertuzumab inhibits the dimerization of HER2 with other HER receptors The antibody may be specific for CD30. CD30 a cell membrane protein of the tumor necrosis factor receptor family and a tumor marker for lymphoma such as Hodgkin lymphoma (HL) and systemic anaplastic large cell lymphoma (sALCL). Preferably, the CD30-specific antibody is Brentuximab vedotin.

The antibody may be specific for GD2. GD2 is a disialoganglioside expressed on tumors of neuroectodermal origin, including human neuroblastoma and melanoma, with highly restricted expression on normal tissues, principally to the cerebellum and peripheral nerves in humans. Preferably, the GD2-specific antibody is Dinutuximab.

The antibody may be specific for VegfR. VegfR is a receptor for endothelial growth factor (VEGF), an important signaling protein involved in both vasculogenesis (the formation of the circulatory system) and angiogenesis (the growth of blood vessels from pre-existing vasculature). Preferably, the anti-VEGFR antibody is Ramucirumab. By binding to VEGFR2, Ramucirumab works as a receptor antagonist blocking the binding of VEGF to VEGFR2.

The antibody may be specific for a tumour antigen. The antibody may be specific for an antigen associated with an infectious agent, such as a virus, a bacteria or a protozoa.

The cytoplasmic domain of the FcR receptor may comprise an activation domain. The activation domain serves to activate the T cell following engagement of the extracellular domain. For instance, the cytoplasmic domain may comprise one or more of a 41BB activation domain, a CD3ζ activation domain and a CD3e activation domain. Preferably, the cytoplasmic domain comprises a 41BB activation domain and/or a CD3ζ activation domain.

The transmembrane domain of the FcR receptor serves to transmit activation signals to the cytoplasmic signal transduction get domains following ligand binding of the extra cellular domains uptown Fc binding. The transmembrane domain may be derived from a molecule other than IgG. Use of a transmembrane domain from a molecule other than IgG avoids problems of antigenicity associated with transmembrane domains derived from IgG. The transmembrane domain may comprise a CD8 activation domain.

The FcR may comprise a spacer. The spacer connects the transmembrane domain to the extracellular domain. The spacer may confer steric effects that influence the strength of activation and inhibition signaling from the target cell and its surface receptors. The spacer may extend to incorporate an immunoglobulin light chain variable region. When an immunoglobulin light chain variable region is used as the spacer, the spacer facilitates FcR dimerization. In turn, dimerization encourages FcRs to cluster on the cell surface, and activation of the T cell via the cytoplasmic activation domains. This results in a stronger signal.

The nucleic acid sequence encoding the FcR may be introduced to the cord blood T cells using any method known in the art. In particular, the cord blood T cells may be transfected or transduced with the nucleic acid sequence.

The term "transduction" may be used to describe virus mediated nucleic acid transfer. A viral vector may be used to transduce the cell with the one or more constructs. Conventional viral based expression systems could include retroviral, lentivirus, adenoviral and adeno-associated (AAV). Non-viral transduction vectors include transposon based systems including Piggy Bac and Sleeping Beauty systems. Methods for producing and purifying such vectors are known in the art. The vector is preferably a vector of the invention. The cord blood T cells may be transduced using any method known in the art. Transduction may be in vitro or ex vivo.

The term "transfection" may be used to describe non-virus-mediated nucleic acid transfer. The cord blood T cells may be transfected using any method known in the art. Transfection may be in vitro or ex vivo. Any vector capable of transfecting the cord blood T cells may be used, such as conventional plasmid DNA or RNA transfection. A human artificial chromosome and/or naked RNA may be used to transfect the cell with the nucleic acid sequence or nucleic acid construct. Human artificial chromosomes are described in e.g. Kazuki et al., Mol. Ther. 19(9): 1591-1601 (2011), and Kouprina et al., Expert Opinion on Drug Delivery 11(4): 517-535 (2014). Alternative non-viral delivery systems include DNA plasmids, naked nucleic acid, and nucleic acid complexed with a delivery vehicle, such as a liposome. Methods of non-viral delivery of nucleic acids include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. The preparation of lipid: nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946, 787).

Nanoparticle delivery systems may be used to transfect the cord blood T cells with the nucleic acid sequence or nucleic acid construct. Such delivery systems include, but are not limited to, lipid-based systems, liposomes, micelles, microvesicles and exosomes. With regard to nanoparticles that can deliver RNA, see, e.g., Alabi et al., Proc Natl Acad Sci USA. 2013 Aug. 6; 110(32): 12881-6; Zhang et al., Adv Mater. 2013 Sep. 6; 25(33): 4641-5; Jiang et al., Nano Lett. 2013 Mar. 13; 13(3): 1059-64; Karagiannis et al., ACS Nano. 2012 Oct. 23; 6(10): 8484-7; Whitehead et al., ACS Nano. 2012 Aug. 28; 6(8): 6922-9 and Lee et al., Nat Nanotechnol. 2012 Jun. 3; 7(6): 389-93. Lipid Nanoparticles, Spherical Nucleic Acid (SNA™) constructs, nanoplexes and other nanoparticles (particularly gold nanoparticles) are also contemplated as a means for delivery of a construct or vector in accordance with the invention.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectAmine, fugene and transfectam.

The cord blood T cells may be transfected or transduced under suitable conditions. For instance, the cord blood T cells may be transfected or transduced following activation with combinations of antibodies such as anti-CD3 and anti-CD28 which may be conjugated to beads or polymers and used with or without cytokines such as IL2, IL7, and IL15. The cord blood T cells and agent or vector may, for example, be contacted for between five minutes and ten days, preferably from an hour to five days, more preferably from five hours to two days and even more preferably from twelve hours to one day after activation.

The nucleic acid sequence transduced or transfected into the cord blood T cells gives rise to expression of FcR in the T cells. If the nucleic acid sequence is transduced into the cord blood T cell, the vector used for transduction may comprise a further nucleic acid sequence encoding another molecule useful to the generation of U-ACT. In particular, and as set out below, CRISPR guide sequences targeting a gene associated with TCR or MHC class I expression or other genomic targets may be present in the same vector as the nucleic acid sequence encoding the FcR.

To make the FcR-expressing cord blood T cells universal, their expression of TCR and MHC class I is disrupted. Mechanisms known in the art for disrupting these molecules include genome editing using zinc finger nucleases (ZFNs), Meganucleases, transcription activator-like effector nucleases (TALENs), or the clustered regularly interspaced short palindromic repeats (CRISPR)/Cas system. All of these genome editing methods can disrupt a gene, entirely knocking out all of its output.

The terminal CRISPR approach described above is used to disrupt expression of TCR and/or MHC class 1. For instance, terminal CRISPR may be used to disrupt expression of TCR. Terminal CRISPR may be used to disrupt expression of MHC class 1. Terminal CRISPR may be used to disrupt expression of TCR and MHC class 1. Terminal CRISPR may be used to disrupt expression of TCR, and ZFNs, TALENS or CRISPR may be used to disrupt expression of MHC class 1. Terminal CRISPR may be used to disrupt expression of MHC class 1, and ZFNs, TALENS or CRISPR may be used to disrupt expression of TCR.

Irrespective of the method used to disrupt TCR expression, TCR expression may be disrupted by targeting one or more of the T cell receptor alpha constant (TRAC) locus, TCR beta constant locus, or CD3 receptor complex chains. The TCR beta constant locus may be C1 or C2. Preferably, the TRAC locus is targeted.

Likewise, MHC class 1 may be disrupted by targeting the transporter associated with antigen processing (TAP1 or TAP2) locus, whichever method of disruption is used. The TAP1 locus may be targetted. MHC class 1 may be disrupted by Beta-2 microglobulin ($\beta_2$m) locus, whichever method of disruption is used. Preferably, the $\beta_2$m locus is targeted. MHC class II molecules may also be disrupted by targeting transcription factors controlling MHC expression such as CIITA, RFX5, RFXAP or RFXANK.

EXAMPLES

Example 1—Cloning of U6 Variants

Materials and Methods

Deletions were made within the hU6 pol III promoter, removing either essential promoter elements or the positional nucleosome sequence. These deletions were made by PCR amplification of the terminal-U6TRAC-CAR19 vector away from the desired site of deletion. Primers were designed using the NEB base changer online tool (http://nebasechanger.neb.com/).

Amplification was performed using Q5® high-fidelity DNA polymerase (M0491S, NEW ENGLAND BioLabs). These PCR products were run on an agarose gel to confirm size, extracted using QIAquick gel extraction kit (28704, QIAGEN) and purified by QIAquick PCR purification kit (28104, QIAGEN). Purified DNA (50 ng) was phosphorylated by T4 Polynucleotide Kinase (M0201S, NEW ENGLAND BioLabs) before a 20 µl ligation at room temperature for 15 minutes by T4 DNA ligase (EL0011, ThermoFisher Scientific) prior to bacterial transformation.

Results

Figure 3:
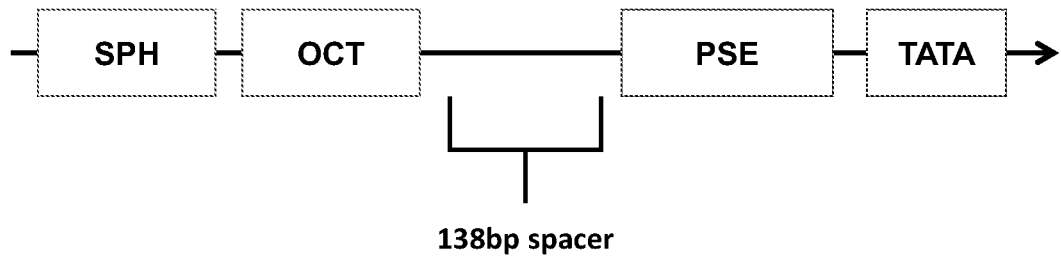
FIG. 3—Terminal lentiviral vector configurations with AU6 Pol III promoters, as considered in Examples 1 and 2.
Figure 3:
Figure 3:
Figure 3:
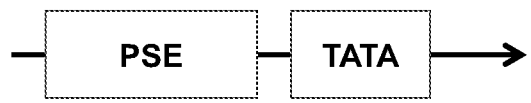
Figure 3:
Figure 3:
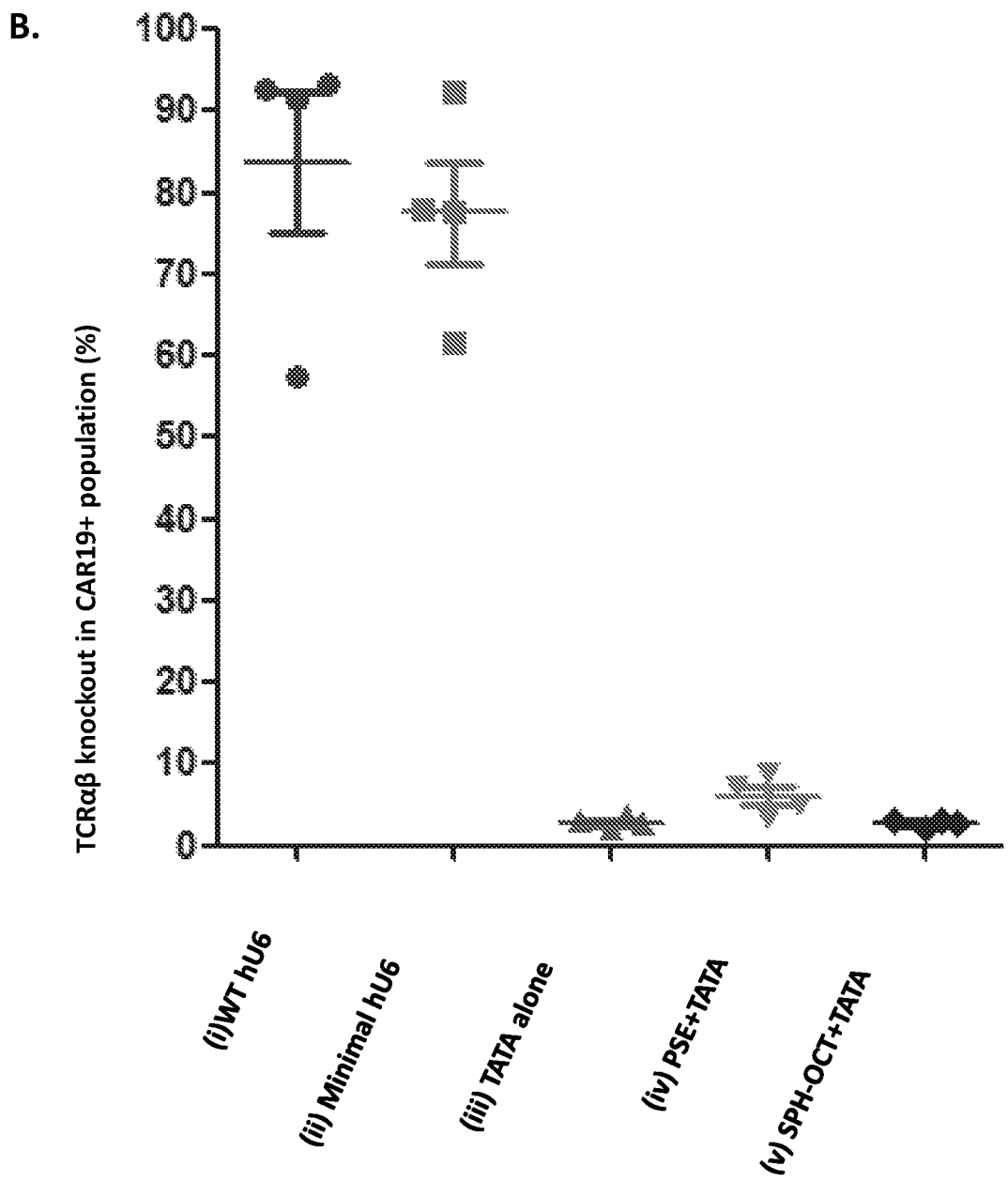
Figure 4:
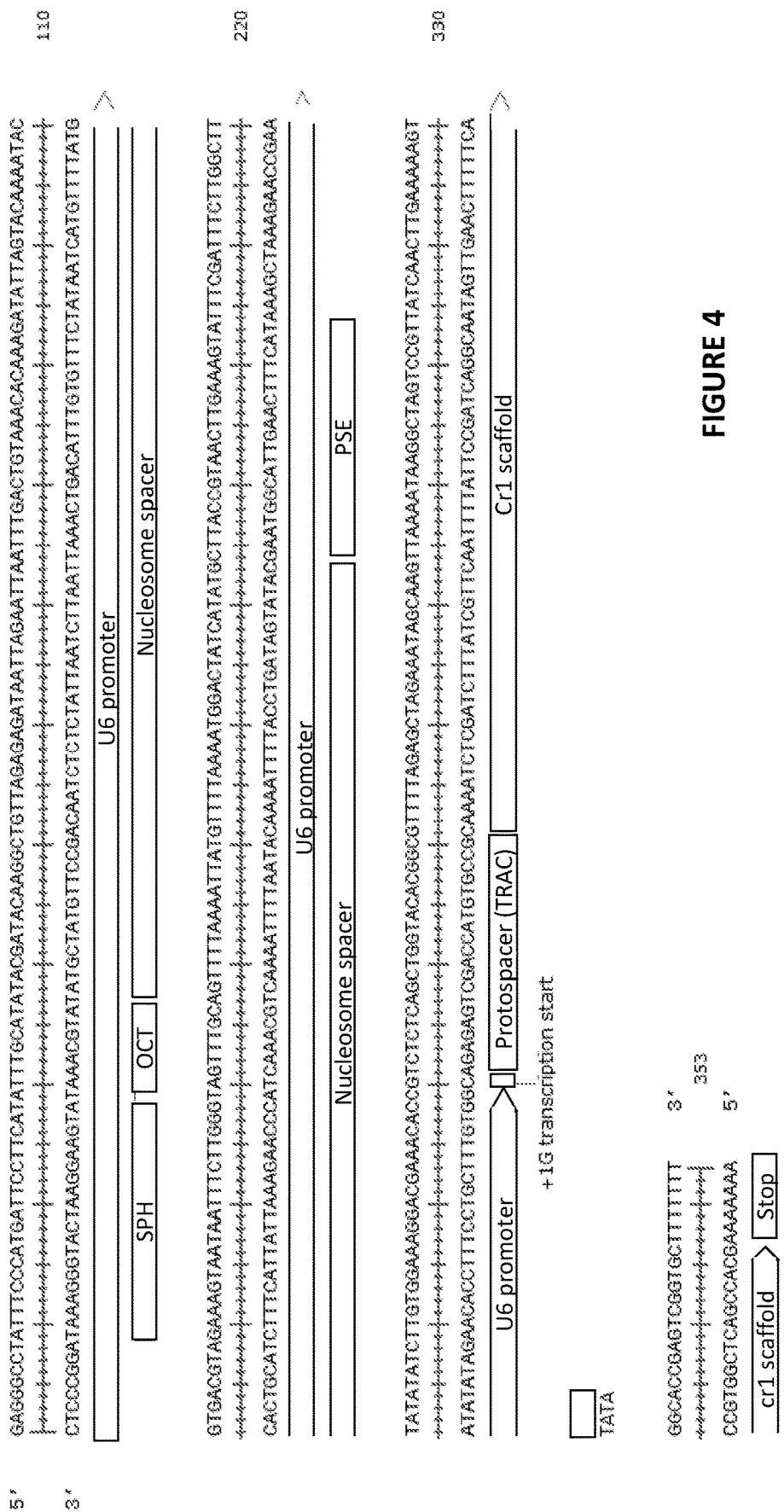
FIG. 4—Wild type U6 expressing CRISPR guide: 353 bp total of which U6 is 249 bp (SEQ ID NO:15).

FIG. 3A provides details the DNA structure of the wild type U6 promoter (i), as well as AU6 promoters (ii-v) containing different deletions created in accordance with the method set out above.

Example 2—Functional Assessment of AU6 Variants

Materials and Methods

Peripheral blood mononuclear cells (PBMCs) were isolated by ficoll density gradient from four donors and subsequently activated with TransACT reagent (130-111-160, Miltenyi Biotech, Surrey, UK). Lymphocytes were cultured in TexMACS medium (130-097-196, Miltenyi Biotech) with 3% human AB serum (GEM-100-512-HI, Seralabs, Brussels, Belgium) and 100 U/ml Proleukin IL-2 (Novartis, Surrey, UK). Transduction with lentiviral vector was performed day 1 after activation at a multiplicity of infection (MOI) of 5. CleanCap™ spCas9 mRNA (TriLink biotechnologies, San Diego, USA) was electroporated day 4 post activation (50 µg/ml), using protocol 24 on the Neon transfection system (ThermoFisher Scientific). Cells were incubated in a state of hypothermia at 30° C. overnight after electroporation before restoration to 37° C. At day 11 post activation cells were stained for CAR19 expression using a Biotin-SP (long spacer) AffiniPure F(ab') Fragment Goat Anti-Mouse IgG, F(ab') Fragment Specific antibody (115-066-072-JIR, Stratech Scientific Limited, Suffolk, UK) followed by Streptavidin-PE (130-106-789, Miltenyi Biotech). This was follow by staining with TCRαβ-APC (130-091-237, Miltenyi Biotech) before cell acquisition on a 4-laser BD LSRII (BD Biosciences, Oxford, UK). Comparison of TCRαβ-CD3 complex removal from the cell surface was normalised between the different construct based on CAR19 expression.

Non parametric Man-Whitney U test was used for comparison between wtU6 and minimal-U6. Statistical analysis was performed using GraphPad Prism software version 5.01.

Results

FIG. 3B shows AU6 promoters tested in a terminal lentiviral vector configuration expressing a TRAC specific sgRNA. These configurations were tested in four primary T cells donors. Results were compared to a terminal lentiviral vector expressing a TRAC sgRNA from the wild type U6 promoter. AU6 promoters containing deletions of the PSE or SPH-OCT domains (iii, iv, and v), showed no CRISPR knockout upon electroporation with spCas9 mRNA. However, minimal U6 promoter with deletion of the functional nucleosome spacer (ii) showed comparable CRISPR knockout to that seen when using the wild type promoter. No significant difference was observed using a non-parametric Mann-Whitney U test.

Figure 6:
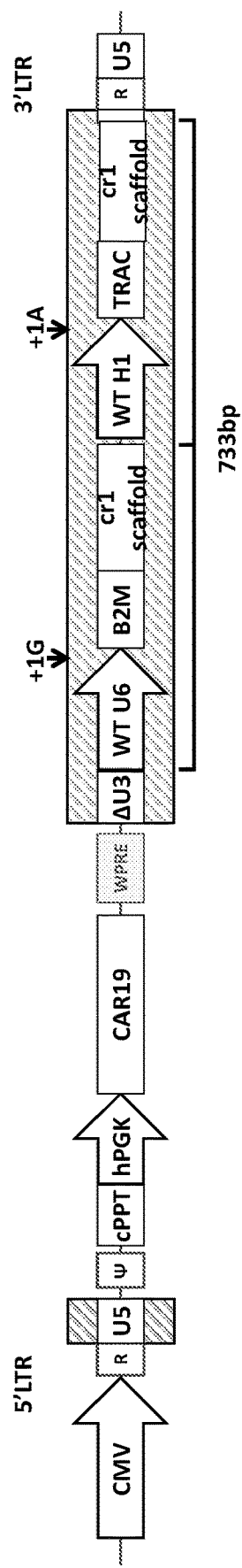
FIG. 6—Multiplex Terminal lentiviral vector containing identical cr1 scaffold sequences results in molecular aberrations during reverse transcription, as considered in Example 3.
Figure 6:
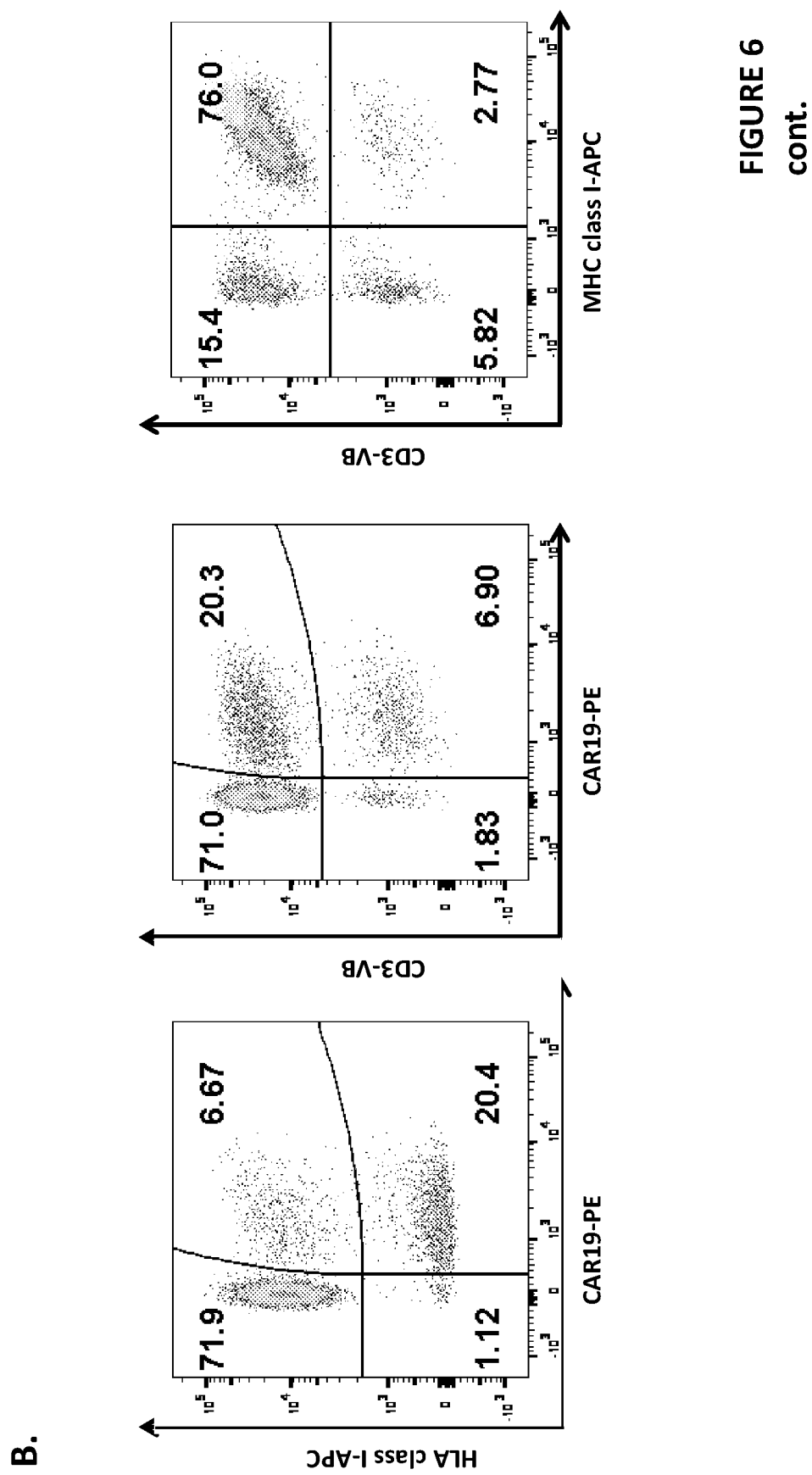
Figure 6:
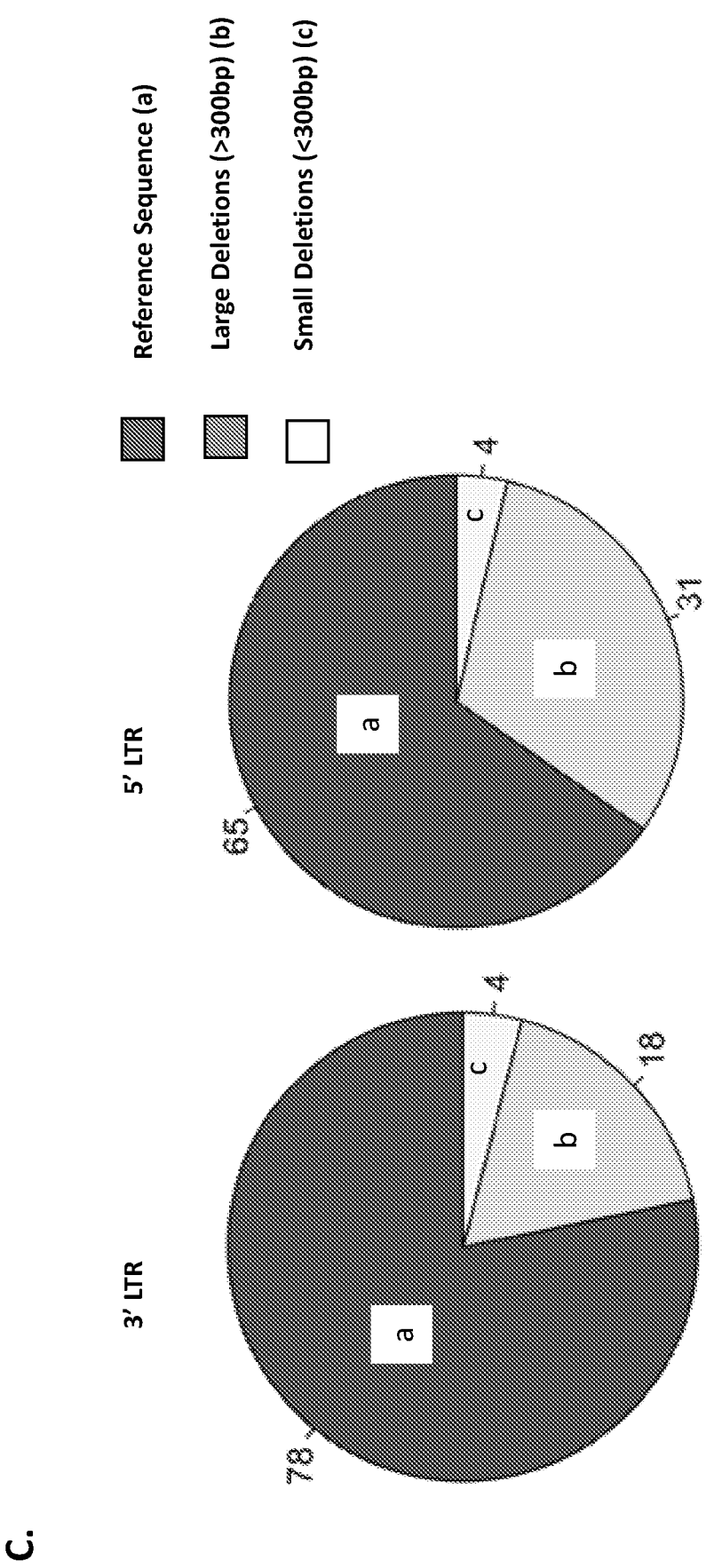

Example 3—Multiplex Terminal Lentiviral Vector Containing Identical cr1 Scaffold Sequences Results in Molecular Aberrations During Reverse Transcription A terminal lentiviral vector containing two CRISPR expression cassettes was created, expressing either a beta-2-microglobulin (B2M) sgRNA or a TRAC sgRNA. The B2M and TRAC sgRNA are expressed from wild type U6 and wild type H1 Pol III promoters respectively. The structure of the vector is shown in FIG. 6A. +1G and +1A act as transcription start sites from U6 and H1 promoters. Both expression cassettes contain an identical cr1 scaffold sequence to allow interaction with the spCas9 endonuclease.

Primary human T cells transduced with multiplex terminal CRISPR vector configuration shown in FIG. 6A at MOI 5 were subjected to flow cytometry based phenotyping. Cells were electroporated with 100 µg/ml spCas9 mRNA and assessed for knockout of both the major histocompatibility complex (MHC) class I, and the TCRαβ-CD3 complex. Results are shown in FIG. 6B. Knockout of B2M and TRAC appeared skewed showing 20.4% B2M knockout compared to 6.9% TRAC knockout.

Next generation sequencing (NGS) for the proviral LTRs was performed to confirm deletions within the LTR sequences between the identical cr1 scaffolds (Large deletions are defined as a complete deletion of the second CRISPR expression cassette between the two cr1 scaffold sequences). Results are shown in FIG. 6C.

Figure 7:
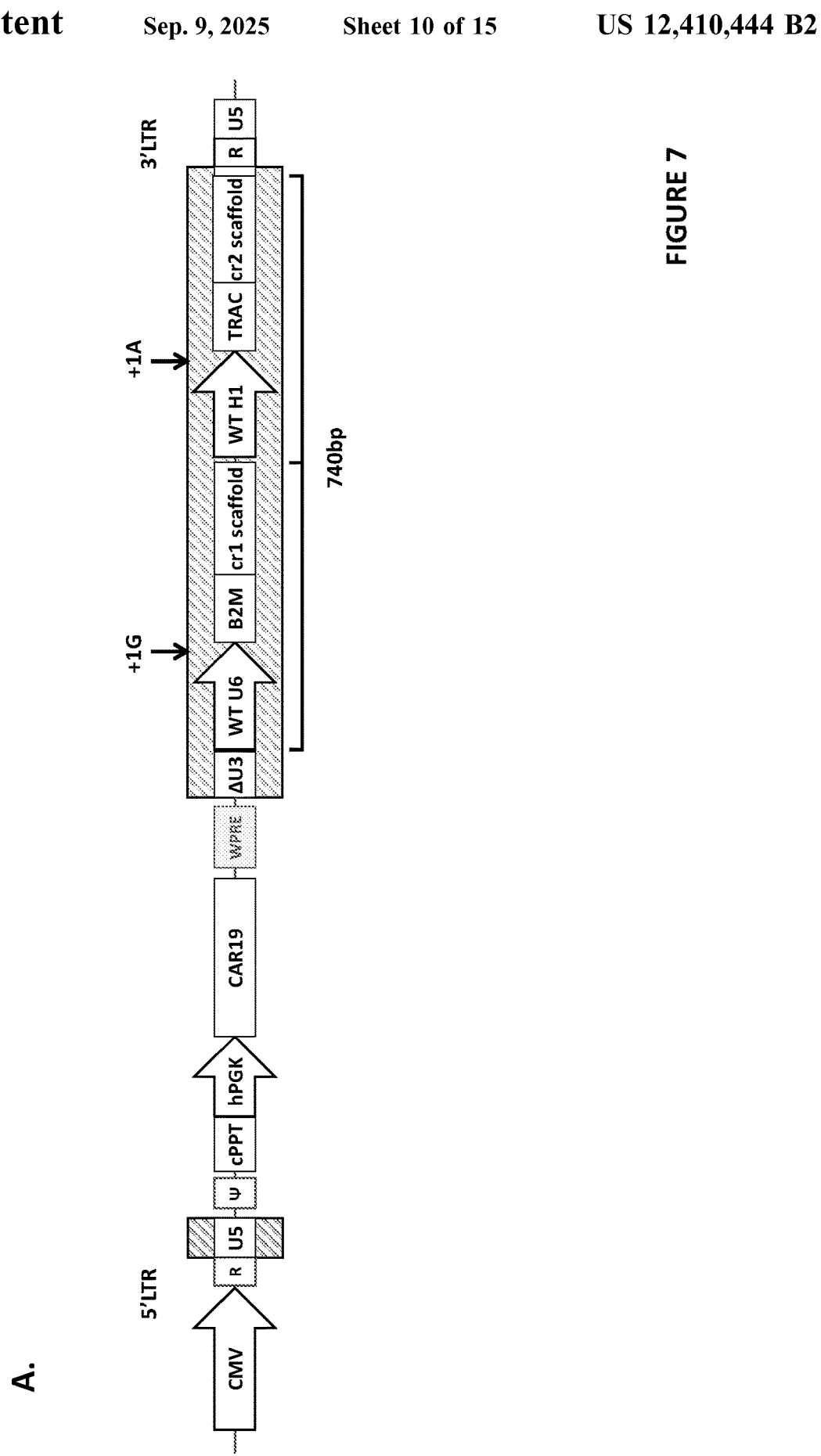
FIG. 7—Multiplex Terminal lentiviral vector configuration incorporating a cr2 scaffold sequence, as considered in Example 4.
Figure 7:
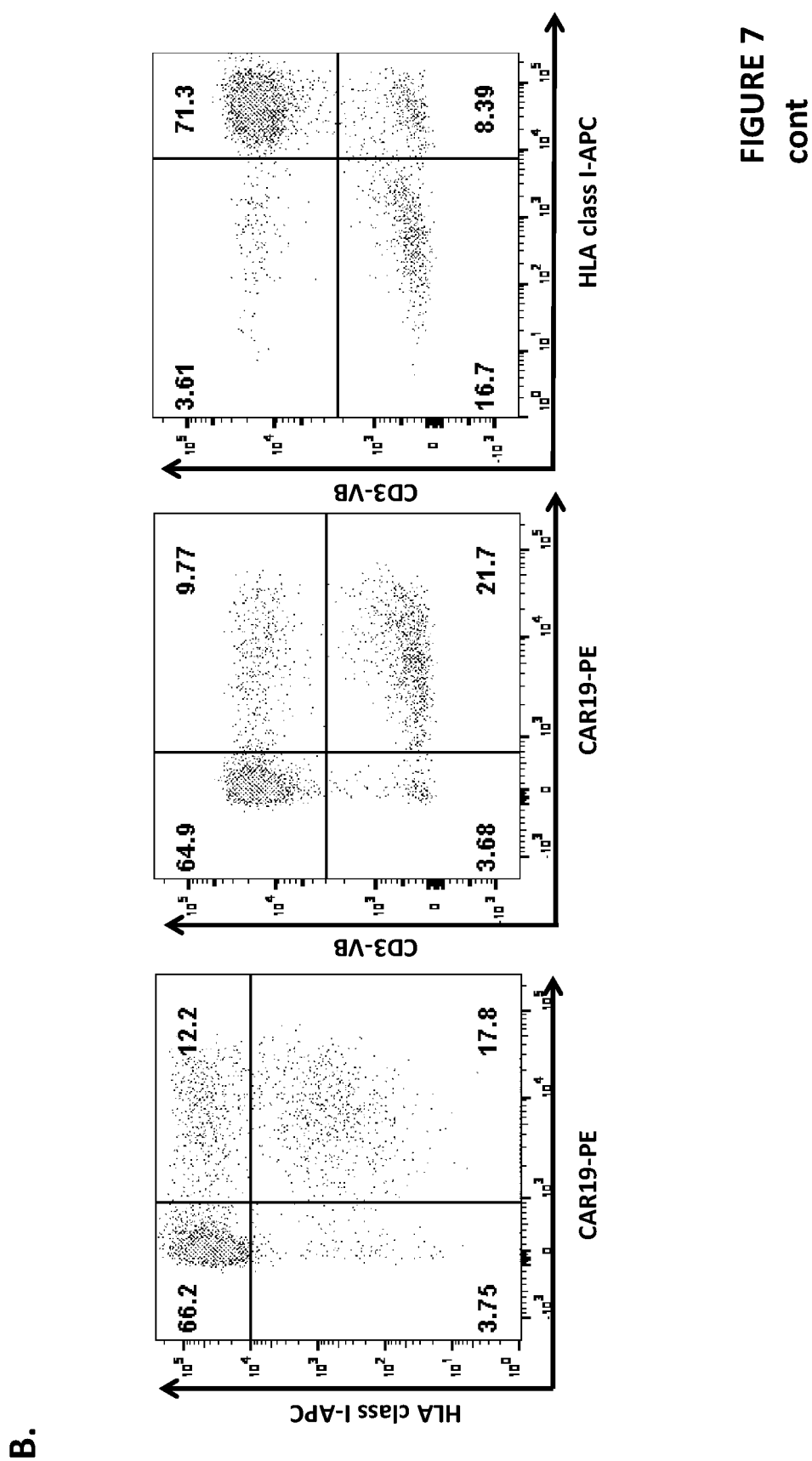
Figure 7:
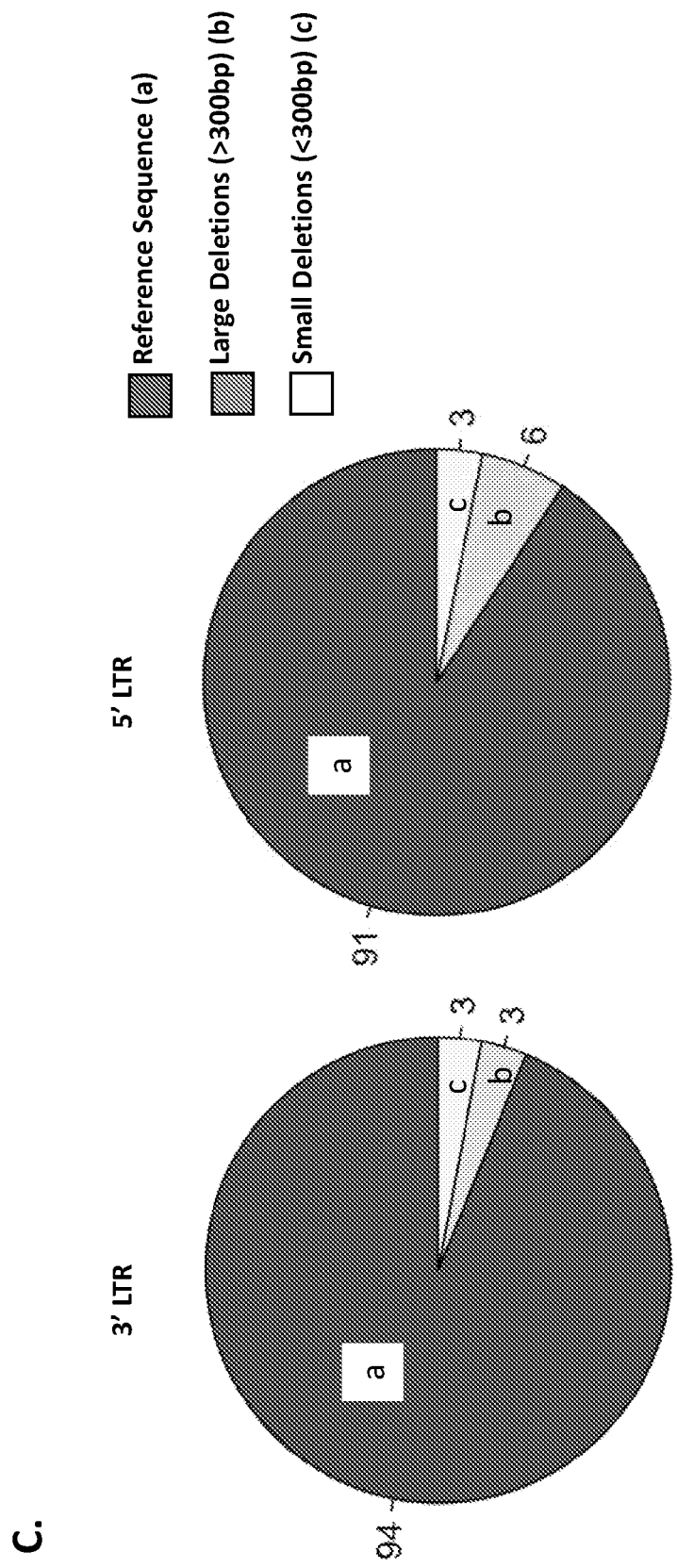

Example 4—Multiplex Terminal Lentiviral Vector Configuration Incorporating a cr2 Scaffold Sequence A terminal lentiviral vector containing two CRISPR expression cassettes was created, expressing either a B2M sgRNA or a TRAC sgRNA. The structure of the vector is shown in FIG. 7A. The B2M and TRAC sgRNA are expressed from wild type U6 and wild type H1 Pol III promoters respectively. +1G and +1A act as transcription start sites for U6 and H1 promoters. Alternative scaffold sequence (cr2) has been incorporated into the second CRISPR expression cassette, to reduce the amount of repetitive sequence (described by Adamson et al., 2016). These CRISPR expression cassettes make up a 740 bp insert in the 3'LTR.

Primary T cells were transduced at MOI 5 with the multiplex terminal vector shown in FIG. 7A. These cells were then electroporated with spCas9 mRNA resulting in a double knockout population of 16.7% (51% of the transduced CAR19+ population). Results of flow cytometry based phenotyping are shown in FIG. 7B.

NGS was performed for the proviral LTR sequences. Results are shown in Figure e7C. The frequency of large deletions appears reduced with the addition of a cr2 scaffold sequence.

Figure 5:
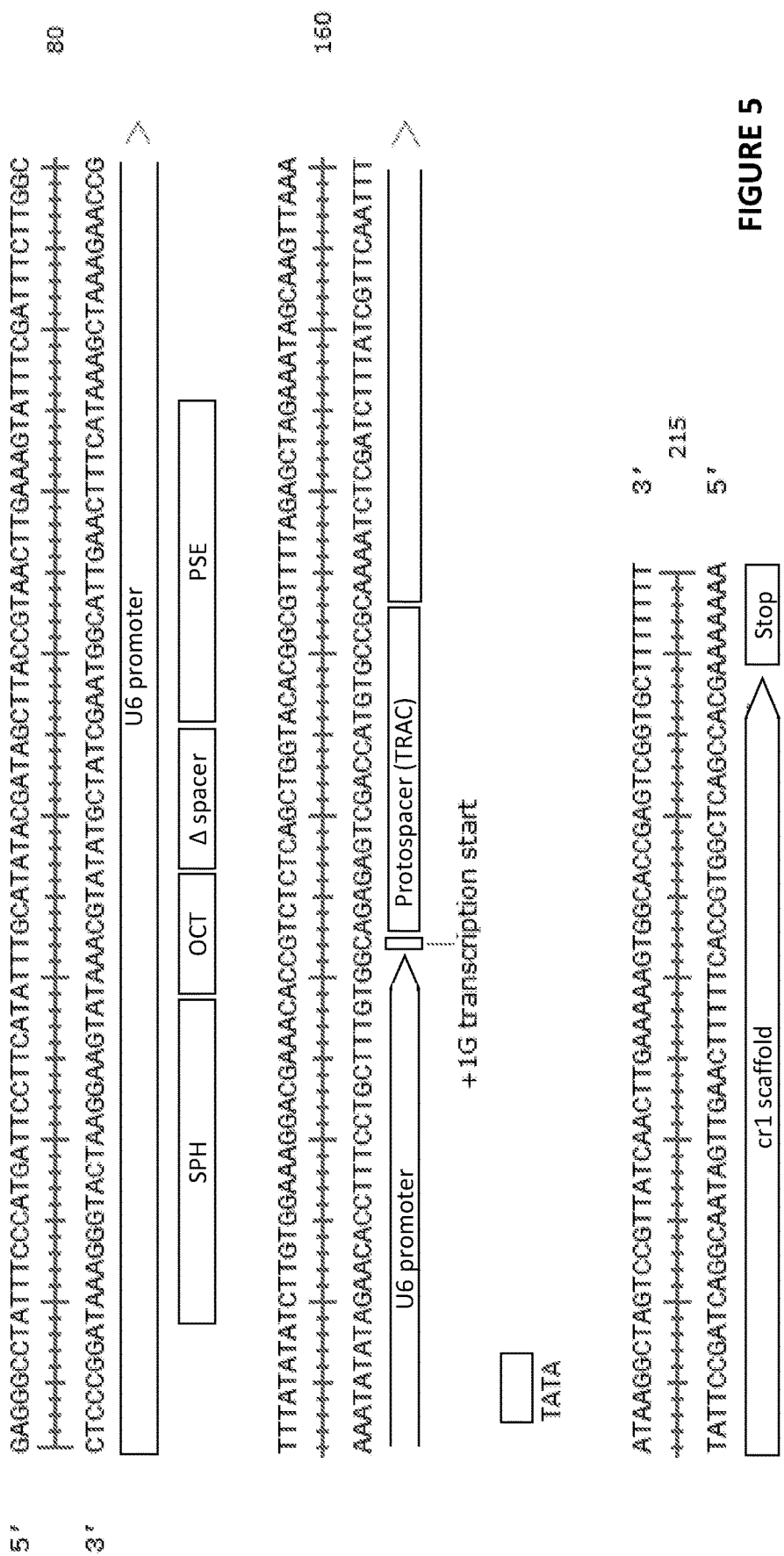
FIG. 5—Mini-U6 expressing CRISPR guide: 215 bp total of which U6 is 111 bp (SEQ ID NO: 16).
Figure 8:
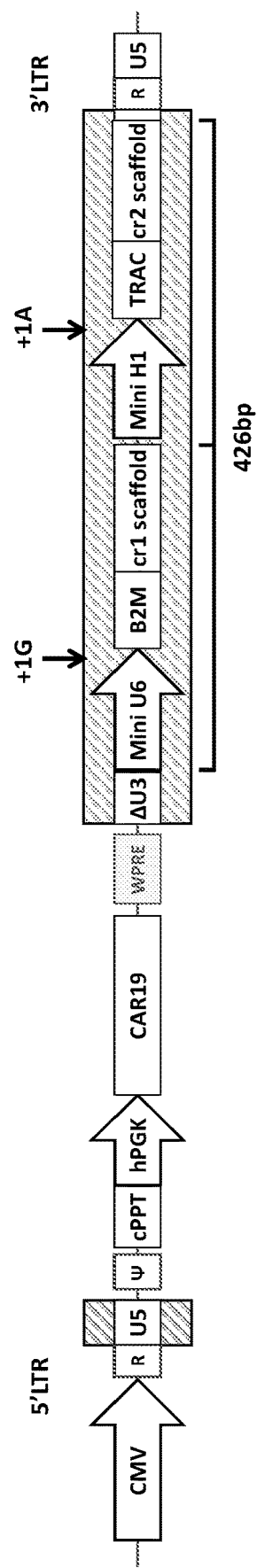
FIG. 8—Multiplex Terminal lentiviral vector configuration with minimal pol III promoters, as considered in Example 5.
Figure 8:
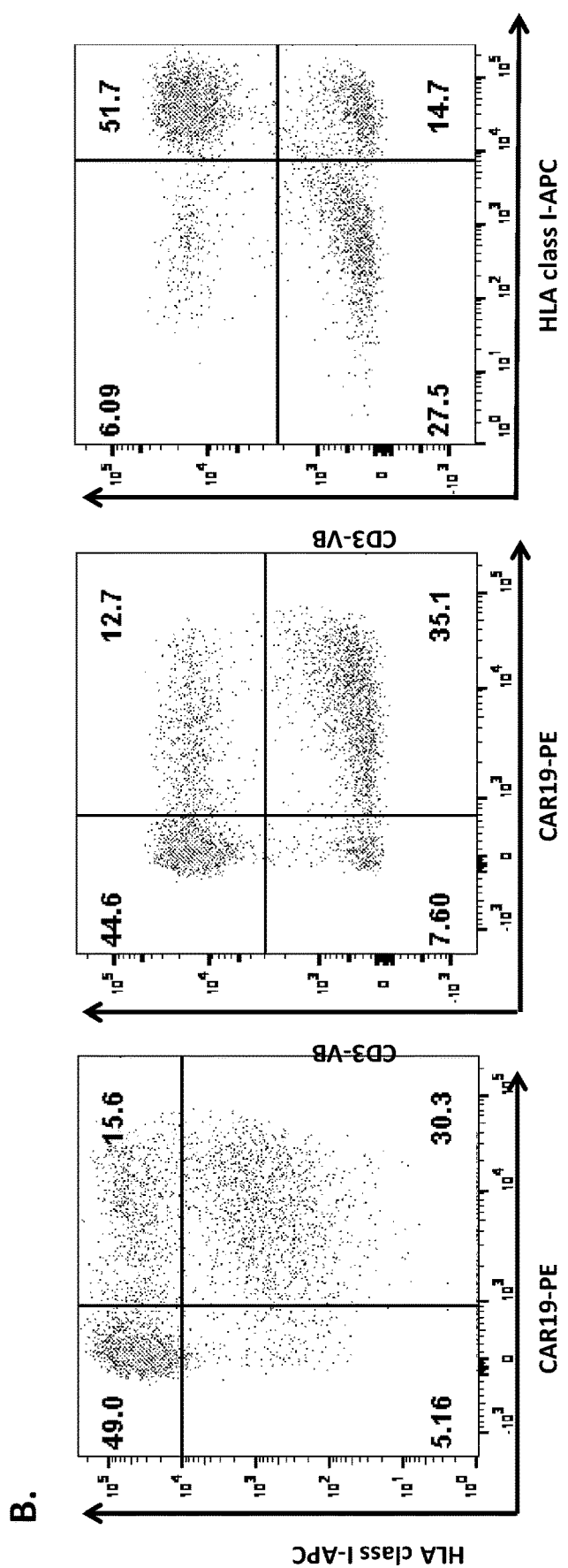
Figure 8:
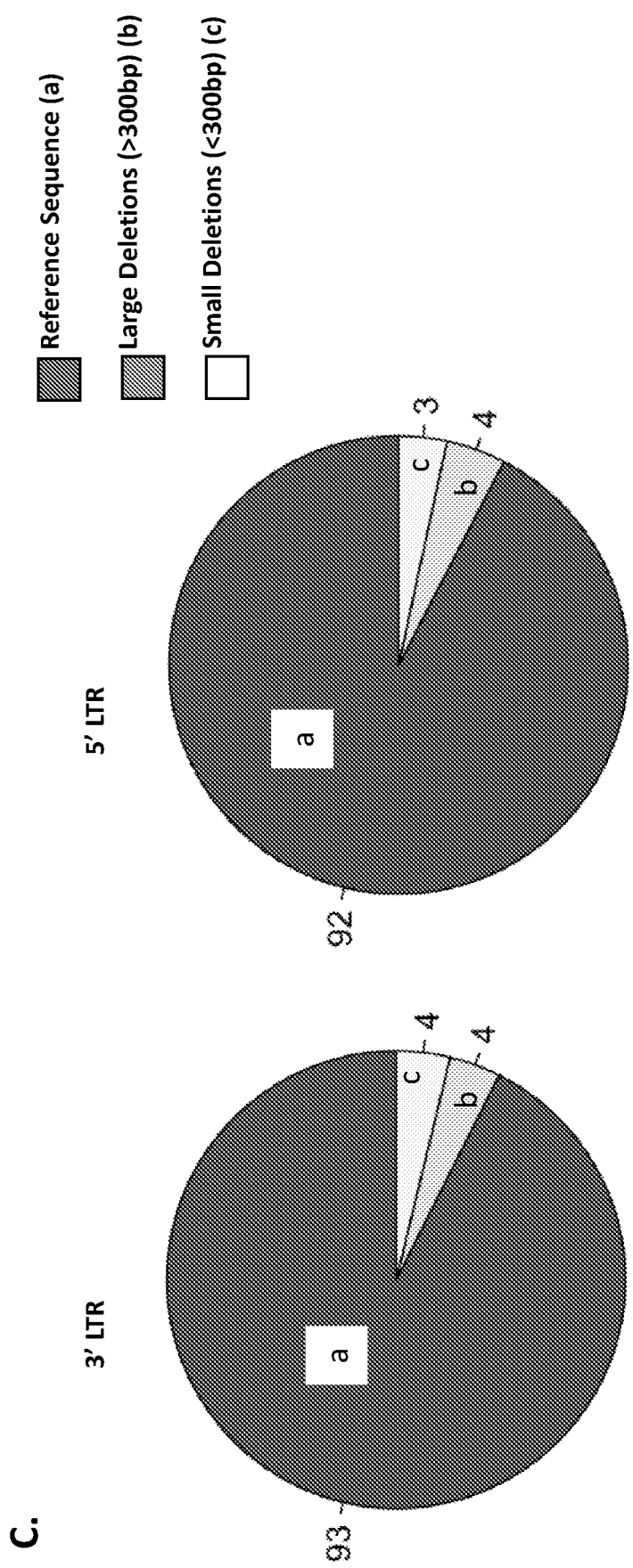

Example 5—Multiplex Terminal Lentiviral Vector Configuration with Minimal Pol III Promoters A terminal lentiviral vector containing two CRISPR expression cassettes was created, having a configuration similar to that considered in Example 4, except that the minimal U6 promoter shown in FIG. 5 and a minimal H1 promoter (Myslinski et al., 2001) were used. Use of these minimal promoters reduces the size of the CRISPR expression cassettes by >42%. The structure of the vector is shown in FIG. 8A. Primary T cells were transduced at MOI 5 with the multiplex configuration containing both minimal U6 and minimal H1 promoters, expressing B2M and TRAC sgRNA. These cells were electroporated with spCas9 mRNA resulting in a doublenegative population of 27.5% (55% of the transduced CAR19+ population). Results of flow cytometry based phenotyping are shown in FIG. 8B. Knockout frequencies appear similar when using a multiplex terminal vector containing full length wild type promoters suggesting retention of promoter function with a highly reduced cassette size.

NGS was performed for the proviral LTR sequences. The frequency of large deletions appears reduced with the addition of a cr2 scaffold sequence (FIG. 8C), similar to the multiplex configuration containing full length wild type pol III promoters with incorporation of a cr2 scaffold sequence.

Materials and Methods for Examples 3, 4 and 5

Multiplex Configuration Knockout

PBMC isolation, activation, and culture were performed as described under slide 4B. As before transduction with the multiplex vector was perform day 1 post activation at MOI5 with electroporation of CleanCap™ spCas9 mRNA (TriLink biotechnologies, San Diego, USA) on day 4 post activation (100 µg/ml). This was again done using program 24 on the Neon transfection system (ThermoFisher Scientific), with subsequent FACS analysis on day 11 post activation. CAR19 transgene staining was performed using a Biotin-SP (long spacer) AffiniPure F(ab') Fragment Goat Anti-Mouse IgG, F(ab') Fragment Specific antibody (115-066-072-JIR, Stratech Scientific Limited, Suffolk, UK) followed by Streptavidin-PE (130-106-789, Miltenyi Biotech). Following this primary antibodies against CD3-VioBlue (130-114-519, Miltenyi Biotech), and MHC Class I-APC (311410, BioLegend, London, UK) were utilised.

Proviral LTR NGS

Genomic DNA was isolated using DNeasy Blood and Tissue Kit (69504, QIAGEN) from cells transduced with each multiplex configuration. Primers were designed to amplify both 3' and 5' proviral LTRs. 3'LTR was amplified using a WPRE forward primer (5' GGACGTCCTTCTGC-TACGTC 3' (SEQ ID NO:22)) and a U5 reverse primers (5' GGGCACACACTACTTGAAGC 3' (SEQ ID NO:23)), while the 5'LTR was amplified using a U3 forward primer (5'GGGCTAATTCACTCCCAACG 3' (SEQ ID NO: 24)) and a Psi reverse primer (5' CTCTCGCACCCATCTCTCTC 3' (SEQ ID NO:25)). Q5® high-fidelity DNA polymerase (M0491S, NEW ENGLAND BioLabs) was used for the PCR reactions. PCR products were library prepped using Illumina's NexteraXT methodology. The pooled libraries were sequenced on UCL Genomic's MiSeq using MiSeq nano 500-V2 kits (Illumina). Quality check was performed on all sequencing data using Phred scores followed by the FastQC tool. Fastq files that had Phred assigning a Q30 score of >70% were further analysed using Pindel, a pattern growth algorithm for detecting large deletions (Ye K, et al. (2009), Bioinformatics, November 1; 25(21): 2865-71). Data were cleaned in their vcf formats in excel and the resulting csv files were read in the programming language R to produce the illustrated pie charts.

REFERENCES

1. Myslinski et al. (2001), Nucleic Acids Res, 2001 Jun. 15; 29(12): 2502-9
2. Zhao et al. (2001), Mol Cell, March; 7(3): 539-49
3. WO 2018/115887
4. Stunkel et al., (1997), Molecular and Cellular Biology, August 4397-4405
5. Gilbert et al. (2013), Cell, July 18; 154(2): 442-451
6. Adamson et al. (2016), Cell, December 15; 167(7): 1867-1882
7. WO 2005/007875
8. Myslinksi et al. (1992), Nucleic Acids Research; 20(2): 203-209
9. Domitrovich and Kunkel (2003), Nucleic Acids Research; 31(9): 2344-2352

The invention claimed is:

1. A U6 pol III promoter that is 74 bp to 117 bp in length and which comprises, from 5' to 3', a distal sequence element (DSE), a proximal sequence element (PSE) and a TATA box, wherein the DSE is connected to the PSE by a DNA spacer sequence that has the sequence of SEQ ID NO: 12.

2. The U6 pol III promoter of claim 1, wherein the U6 pol III promoter is up to 111 bp in length.

3. The U6 pol III promoter of claim 1, wherein the PSE is connected to the TATA box by a spacer sequence that is 40 bp or less in length, optionally wherein the spacer sequence connecting the PSE to the TATA box is 17 bp or less in length.

4. The U6 pol III promoter of claim 1, wherein the promoter comprises a spacer sequence of 22 bp to 35 bp in length 3' of the TATA box, optionally wherein the spacer sequence 3' of the TATA box is 22 bp to 25 bp in length.

5. The U6 pol III promoter of claim 1, wherein the DSE is 28 bp in length.

6. The U6 pol III promoter of claim 1, wherein the PSE is 20 bp in length.

7. The U6 pol III promoter of claim 1, wherein the DSE has a sequence identical to a DSE sequence from a human U6 pol III promoter.

8. The U6 pol III promoter of claim 1, wherein the PSE has a sequence identical to a PSE sequence from a human U6 pol III promoter.

9. The U6 pol III promoter of claim 1, wherein the DSE comprises or consists of the sequence of SEQ ID NO: 2.

10. The U6 pol III promoter of claim 1, wherein the PSE comprises or consists of the sequence of SEQ ID NO: 6.

11. The U6 pol III promoter of claim 1, wherein the U6 pol III promoter comprises or consists of:
   (i) the sequence of SEQ ID NO: 8; or
   (ii) a sequence that comprises from 5' to 3' the sequence of SEQ ID NO: 2, the sequence of SEQ ID NO: 6 and a TATA sequence, and that has at least 90% identity over its entire length to SEQ ID NO: 8.

12. A nucleic acid construct comprising the U6 pol III promoter of claim 1.

13. The nucleic acid construct of claim 12, wherein the U6 pol III promoter is comprised in a 3' long terminal repeat region (LTR).

14. The nucleic acid construct of claim 12, wherein the U6 pol III promoter is operably linked to a sequence encoding a CRISPR guide RNA sequence.

15. The nucleic acid construct of claim 14, comprising a cr1 scaffold sequence 3' of the U6 pol III promoter, a cr2 scaffold sequence 3' of the U6 pol III promoter, or a cr3 scaffold sequence 3' of the U6 pol III promoter.

16. A vector comprising the nucleic acid construct of claim 12, optionally wherein the vector is a viral vector.

17. The vector of claim 16, wherein the vector is a lentiviral vector.

* * * * *

SEQUENCE LISTING

<160> NUMBER OF SEQ ID NOS: 25

<210> SEQ ID NO 1
<211> LENGTH: 249
<212> TYPE: DNA
<213> ORGANISM: Homo sapiens

<400> SEQUENCE: 1
gagggcctat ttcccatgat tccttcatat ttgcatatac gatacaaggc tgttagagag      60
ataattagaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacacc                                                             249

<210> SEQ ID NO 2
<211> LENGTH: 28
<212> TYPE: DNA
<213> ORGANISM: Homo sapiens

<400> SEQUENCE: 2
atttcccatg attccttcat atttgcat                                         28

<210> SEQ ID NO 3
<211> LENGTH: 20
<212> TYPE: DNA
<213> ORGANISM: Homo sapiens

<400> SEQUENCE: 3
atttcccatg attccttcat                                                  20

<210> SEQ ID NO 4
<211> LENGTH: 8
<212> TYPE: DNA
<213> ORGANISM: Homo sapiens

<400> SEQUENCE: 4 atttgcat                                                                8

<210> SEQ ID NO 5
<211> LENGTH: 147
<212> TYPE: DNA
<213> ORGANISM: Homo sapiens

<400> SEQUENCE: 5
atacgataca aggctgttag agagataatt agaattaatt tgactgtaaa cacaaagata      60
ttagtacaaa atacgtgacg tagaaagtaa taatttcttg ggtagtttgc agttttaaaa     120
ttatgtttta aaatggacta tcatatg                                         147

<210> SEQ ID NO 6
<211> LENGTH: 20
<212> TYPE: DNA
<213> ORGANISM: Homo sapiens

<400> SEQUENCE: 6
cttaccgtaa cttgaaagta                                                  20

<210> SEQ ID NO 7
<211> LENGTH: 17
<212> TYPE: DNA
<213> ORGANISM: Homo sapiens

```
<400> SEQUENCE: 7
tttcgatttc ttggctt                                                    17

<210> SEQ ID NO 8
<211> LENGTH: 111
<212> TYPE: DNA
<213> ORGANISM: Artificial Sequence
<220> FEATURE:
<223> OTHER INFORMATION: Mini-U6 promoter of Example 5

<400> SEQUENCE: 8
gagggcctat ttcccatgat tccttcatat ttgcatatac gatagcttac cgtaacttga     60
aagtatttcg atttcttggc tttatatatc ttgtggaaag gacgaaacac c             111

<210> SEQ ID NO 9
<211> LENGTH: 28
<212> TYPE: DNA
<213> ORGANISM: Artificial Sequence
<220> FEATURE:
<223> OTHER INFORMATION: DSE of mini-U6 promoter of Example 5

<400> SEQUENCE: 9
atttcccatg attccttcat atttgcat                                        28

<210> SEQ ID NO 10
<211> LENGTH: 20
<212> TYPE: DNA
<213> ORGANISM: Artificial Sequence
<220> FEATURE:
<223> OTHER INFORMATION: SPH of mini-U6 promoter of Example 5

<400> SEQUENCE: 10
atttcccatg attccttcat                                                 20

<210> SEQ ID NO 11
<211> LENGTH: 8
<212> TYPE: DNA
<213> ORGANISM: Artificial Sequence
<220> FEATURE:
<223> OTHER INFORMATION: OCT of mini-U6 promoter of Example 5

<400> SEQUENCE: 11 atttgcat                                                               8

<210> SEQ ID NO 12
<211> LENGTH: 9
<212> TYPE: DNA
<213> ORGANISM: Artificial Sequence
<220> FEATURE:
<223> OTHER INFORMATION: Spacer sequence connecting DSE to PSE in
      mini-U6 promoter of Example 5

<400> SEQUENCE: 12 atacgatag                                                              9

<210> SEQ ID NO 13
<211> LENGTH: 20
<212> TYPE: DNA
<213> ORGANISM: Artificial Sequence
<220> FEATURE:
<223> OTHER INFORMATION: PSE of mini-U6 promoter of Example 5

<400> SEQUENCE: 13
cttaccgtaa cttgaaagta                                                 20
```

<210> SEQ ID NO 14
<211> LENGTH: 17
<212> TYPE: DNA
<213> ORGANISM: Artificial Sequence
<220> FEATURE:
<223> OTHER INFORMATION: Spacer sequence connecting PSE to TATA box in
      mini-U6 promoter of Example 5

<400> SEQUENCE: 14
tttcgatttc ttggctt                                                      17

<210> SEQ ID NO 15
<211> LENGTH: 353
<212> TYPE: DNA
<213> ORGANISM: Artificial Sequence
<220> FEATURE:
<223> OTHER INFORMATION: Wild-type human U6 promoter expressing CRISPR
      guide

<400> SEQUENCE: 15
gagggcctat ttcccatgat tccttcatat ttgcatatac gatacaaggc tgttagagag        60
ataattagaa ttaatttgac tgtaaacaca aagatattag tacaaaatac gtgacgtaga       120
aagtaataat ttcttgggta gtttgcagtt ttaaaattat gttttaaaat ggactatcat       180
atgcttaccg taacttgaaa gtatttcgat ttcttggctt tatatatctt gtggaaagga       240
cgaaacaccg tctctcagct ggtacacggc gttttagagc tagaaatagc aagttaaaat       300
aaggctagtc cgttatcaac ttgaaaaagt ggcaccgagt cggtgctttt ttt             353

<210> SEQ ID NO 16
<211> LENGTH: 215
<212> TYPE: DNA
<213> ORGANISM: Artificial Sequence
<220> FEATURE:
<223> OTHER INFORMATION: Mini-U6 promoter of Example 5 expressing CRISPR
      guide RNA

<400> SEQUENCE: 16
gagggcctat ttcccatgat tccttcatat ttgcatatac gatagcttac cgtaacttga        60
aagtatttcg atttcttggc tttatatatc ttgtggaaag gacgaaacac cgtctctcag       120
ctggtacacg gcgttttaga gctagaaata gcaagttaaa ataaggctag tccgttatca       180
acttgaaaaa gtggcaccga gtcggtgctt ttttt                                  215

<210> SEQ ID NO 17
<211> LENGTH: 20
<212> TYPE: DNA
<213> ORGANISM: Artificial Sequence
<220> FEATURE:
<223> OTHER INFORMATION: Protospacer (TRAC) in the mini-U6 promoter of
      Example 5

<400> SEQUENCE: 17
tctctcagct ggtacacggc                                                   20

<210> SEQ ID NO 18
<211> LENGTH: 76
<212> TYPE: DNA
<213> ORGANISM: Artificial Sequence
<220> FEATURE:
<223> OTHER INFORMATION: cr1 scaffold

<400> SEQUENCE: 18
gttttagagc tagaaatagc aagttaaaat aaggctagtc cgttatcaac ttgaaaaagt    60
ggcaccgagt cggtgc    76

<210> SEQ ID NO 19
<211> LENGTH: 95
<212> TYPE: DNA
<213> ORGANISM: Artificial Sequence
<220> FEATURE:
<223> OTHER INFORMATION: cr2 scaffold

<400> SEQUENCE: 19
gtttgagagc taagcagaaa gctgcatagc aagttcaaat aaggctagtc cgtacacaac    60
ttgaaaaagt ggcagccgag tcggctgctt ttttt    95

<210> SEQ ID NO 20
<211> LENGTH: 95
<212> TYPE: DNA
<213> ORGANISM: Artificial Sequence
<220> FEATURE:
<223> OTHER INFORMATION: cr3 scaffold

<400> SEQUENCE: 20
gtttcagagc taagcacaag agtgcatagc aagttgaaat aaggctagtc cgtttacaac    60
ttgaaaaagt ggcacccgag tcgggtgctt ttttt    95

<210> SEQ ID NO 21
<211> LENGTH: 25
<212> TYPE: DNA
<213> ORGANISM: Artificial Sequence
<220> FEATURE:
<223> OTHER INFORMATION: Sequence 3' of the TATA box in the mini-U6
      promoter of Example 5

<400> SEQUENCE: 21
tatcttgtgg aaaggacgaa acacc    25

<210> SEQ ID NO 22
<211> LENGTH: 20
<212> TYPE: DNA
<213> ORGANISM: Artificial Sequence
<220> FEATURE:
<223> OTHER INFORMATION: WPRE forward primer

<400> SEQUENCE: 22
ggacgtcctt ctgctacgtc    20

<210> SEQ ID NO 23
<211> LENGTH: 20
<212> TYPE: DNA
<213> ORGANISM: Artificial Sequence
<220> FEATURE:
<223> OTHER INFORMATION: U5 reverse primer

<400> SEQUENCE: 23
gggcacacac tacttgaagc    20

<210> SEQ ID NO 24
<211> LENGTH: 20
<212> TYPE: DNA
<213> ORGANISM: Artificial Sequence
<220> FEATURE:
<223> OTHER INFORMATION: U3 forward primer

<400> SEQUENCE: 24

```
gggctaattc actcccaacg                                              20

<210> SEQ ID NO 25
<211> LENGTH: 20
<212> TYPE: DNA
<213> ORGANISM: Artificial Sequence
<220> FEATURE:
<223> OTHER INFORMATION: Psi reverse primer

<400> SEQUENCE: 25
ctctcgcacc catctctctc                                              20
```